US009447407B2

(12) United States Patent
Zink et al.

(10) Patent No.: US 9,447,407 B2
(45) Date of Patent: Sep. 20, 2016

(54) DOUBLE COATING PROCEDURE FOR THE MEMBRANES OF BIOARTIFICIAL KIDNEYS

(75) Inventors: Daniele Zink, Singapore (SG); Ming Ni, Singapore (SG); Jackie Y. Ying, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 307 days.

(21) Appl. No.: 13/019,352

(22) Filed: Feb. 2, 2011

(65) Prior Publication Data

US 2012/0196345 A1    Aug. 2, 2012

(51) Int. Cl.
  *C12N 11/06*   (2006.01)
  *B01D 67/00*   (2006.01)
(52) U.S. Cl.
  CPC ............ *C12N 11/06* (2013.01); *B01D 67/0088* (2013.01)
(58) Field of Classification Search
  CPC ........................... C12N 11/06; B01D 67/0088
  USPC .................................... 435/284.1; 623/23.65
  See application file for complete search history.

(56) References Cited

U.S. PATENT DOCUMENTS

| | | | |
|---|---|---|---|
| 3,859,331 | A | 1/1975 | Kaiser et al. |
| 2009/0209019 | A1 | 8/2009 | Saito et al. |
| 2011/0129924 | A1 | 6/2011 | Ying et al. |
| 2012/0184940 | A1 | 7/2012 | Ying et al. |
| 2012/0202741 | A1 | 8/2012 | Zink et al. |

FOREIGN PATENT DOCUMENTS

| | | |
|---|---|---|
| JP | 2007-527871 | 10/2007 |
| JP | 2010-521246 | 6/2010 |
| JP | 2011-21184 | 10/2014 |
| WO | WO 2005/118831 | 12/2005 |
| WO | WO-2008/005035 A1 | 1/2008 |
| WO | WO 2008/047760 | 4/2008 |
| WO | WO 2008/113005 | 9/2008 |
| WO | WO-2011/040889 A1 | 4/2011 |
| WO | WO-2011/043738 A2 | 4/2011 |

OTHER PUBLICATIONS

Kang et al. "Bioinspired single bacterial cell force spectroscopy", Langmuir, 2009, 25(17):9656-9659.*
Ku et al. "General functionalization route for cell adhesion on non-wetting surfaces", Biomaterials, 2010,31:2535-2541.*
Lee et al. "Mussel-inspired surface chemistry for multifunctional coatings", Science, 2007, 318(5849):1-10.*
Ku et al. "Human endothelial cell growth on mussel-inspried nanofiber scaffold for vascular tissue engineering", Biomaterials, 2010, 31:9431-9437.*
Ozgen et al. "Evaluation of long-term transport ability of a bioartificial renal tubule device using LLC-PK1 cells", Nephrol Dial Transplant, 2004, 19:2198-2207.*

The 5$^{th}$ SBE International Conference on Bioengineering and Nanotechnology, Singapore: Poster presentation on Aug. 3, 2010. Presenter: Ming Ni.
The 5$^{th}$ SBE International Conference on Bioengineering and Nanotechnology, Singapore: Oral conference presentation on Aug. 4, 2010. Presenter: Daniele Zink.
Seminar on Sep. 13, 2010—European Conference on Biomaterials, Tampere Finland. Presenter: Ming Ni.
The 5$^{th}$ SBE International Conference on Bioengineering and Nanotechnology, Singapore: IBN Labtour on Aug. 3, 2010. Presenter: Daniele Zink.
Doraiswamy, Matrix-assisted pulsed-laser evaporation of DOPA-modified poly(ethylene glycol) thin films, *J. Adhesion Sci Technol* (2007) p. 1-13.
Humes et al., Initial clinical results of the bioartificial kidney containing human cells in ICU patients with acute renal failure. *Kidney Int* 66:1578-1588 (2004).
Ku et al.: General functionalization route for cell adhesion on non-wetting surfaces, *Biomaterials*, 31:2535-2541 (2010).
Lee et al.: Mussel-Inspired Surface Chemistry for Multifunctional Coatings, *Science*, 318:426 (2007).
Lee et al., A reversible wet/dry adhesive inspired by mussels and geckos, *Nature*, 448:338 (Jul. 19, 2007).
Lee et al, Single-molecule mechanics of mussel adhesion, *PNAS*, 103, 12999-13003 (Aug. 29, 2006).
Ni et al., Characterization of membrane materials and membrane coatings for bioreactor units of bioartificial kidneys, *Biomaterials*, 32, pp. 1465-1476, 2011.

(Continued)

*Primary Examiner* — Bin Shen
(74) *Attorney, Agent, or Firm* — Wolf, Greenfield & Sacks, P.C.

(57) ABSTRACT

The present invention generally relates to modified substrates such as membranes for use in bioartificial organs, such as bioartificial kidneys, and other applications. Certain aspects are generally directed to a membrane or other substrate modified to facilitate the attachment of cells. In one set of embodiments, the substrate or membrane may be at least partially coated with an adhesive such as 3,4-dihydroxy-L-phenylalanine (DOPA), poly(dopamine), or other adhesive comprising a molecule having a catechol moiety, for example on one side of the membrane or substrate. On at least a portion of the adhesive coated portion of the substrate, a protein may be coated, such as an extracellular matrix protein (for example, a collagen), to which cells such as primary human renal proximal tubule cells may be adhered. Surprisingly, such a dual coating may be used to promote the attachment of such cells to a membrane or other substrate that otherwise may not promote cell adhesion. In certain embodiments, the coating may also facilitate or promote not only cell adhesion, but also cell proliferation and/or differentiation. Such membranes or other substrates may be useful, for example, in bioartificial organs such as bioartificial kidneys, hemodialysis cartridges, bioimplants, biosensors, bioreactors, etc. In certain embodiments, cells may be attached to a membrane or other substrate on only one side, while the other side may be kept free of attached cells.

28 Claims, 9 Drawing Sheets

(56) References Cited

OTHER PUBLICATIONS

Podsiadlo et al., Fusion of seashell nacre and marine bioadhesive analogs: high-strength nanocomposite by layer-by-layer assembly of clay and $_L$-3,4-dihydroxyphenylalanine polymer, *Advanced Materials*, 19:949-955 (2007) (2519).

Tasnim et al., Achievements and challenges in bioartificial kidney development, Fibrogenesis Tissue Repair 3:14, 2011.

Tumlin et al., Efficacy and safety of renal tubule cell therapy for acute renal failure. *J Am Soc Nephrol* 19:1034-1040, 2008.

Ueda et al., Asymmetrically functional surface properties on biocompatible phospholipid polymer membrane for bioartificial kidney. *J. Biomed Mater Res A* 77:19-27, 2006.

Zhang et al.: The impact of extracellular matrix coatings on the performance of human renal cells applied in bioartificial kidneys, Biomaterials, pp. 2899-2911, 2009.

Kandasamy et al., Polysulfone membranes coated with polymerized 3,4-dihydroxy-1-phenylalanine are a versatile and cost-effective synthetic substrate for defined long-term cultures of human pluripotent stem cells. Biomacromolecules. Jun. 9, 2014;15(6):2067-78. Epub May 9, 2014. Includes supporting information.

* cited by examiner

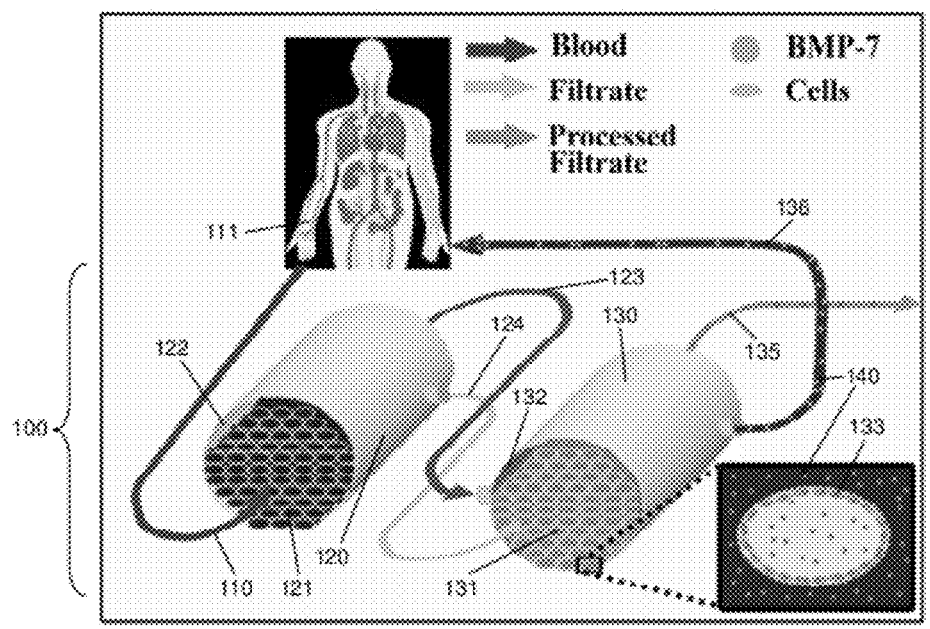
Fig. 1
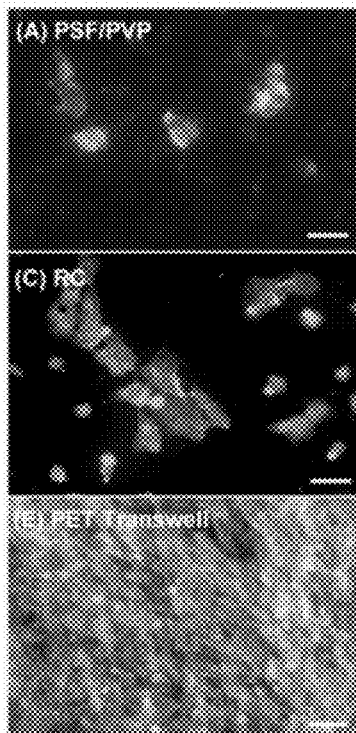
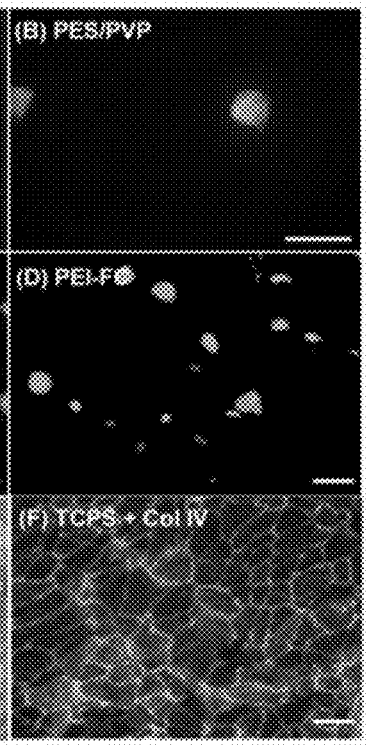
Fig. 2A   Fig. 2B
Fig. 2C   Fig. 2D
Fig. 2E   Fig. 2F

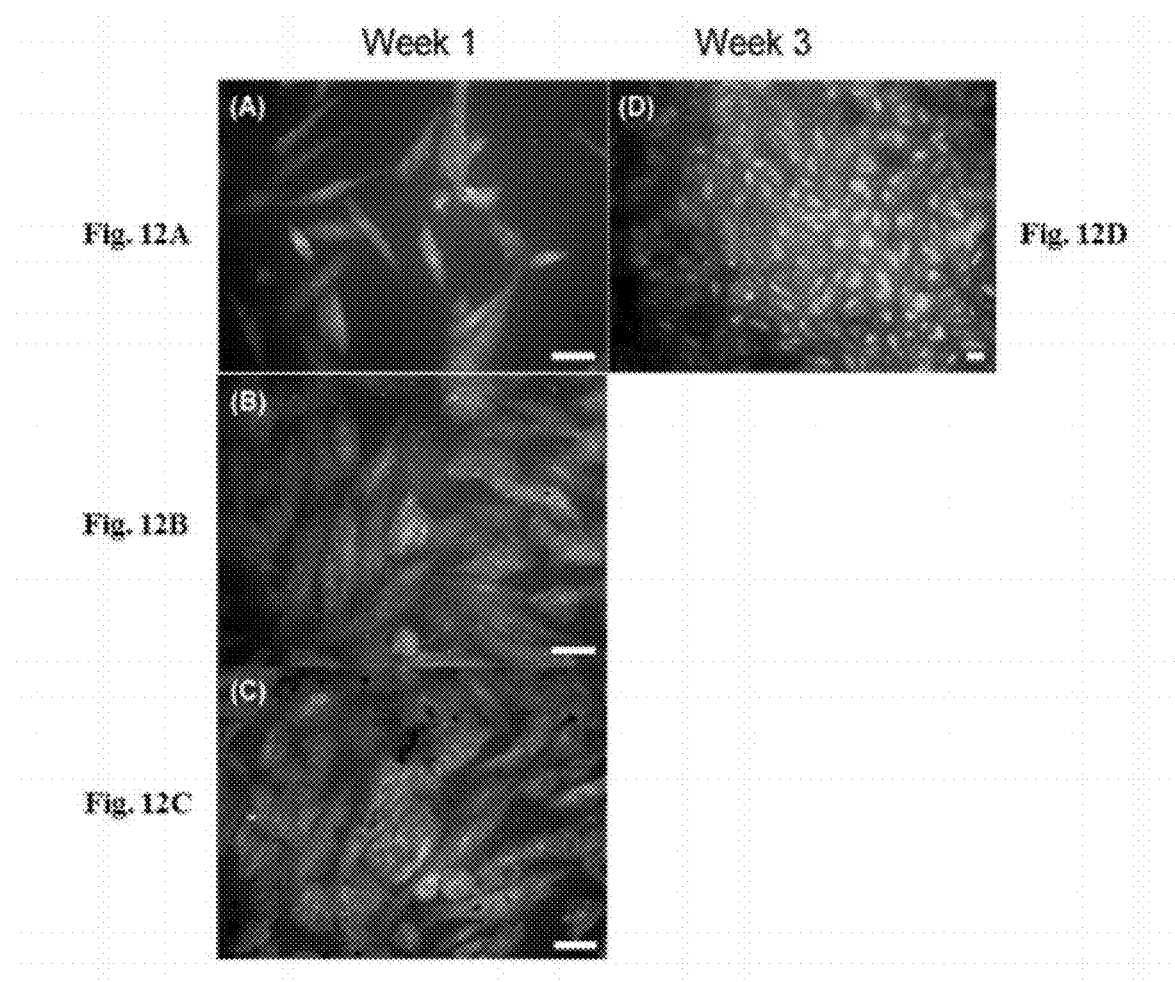

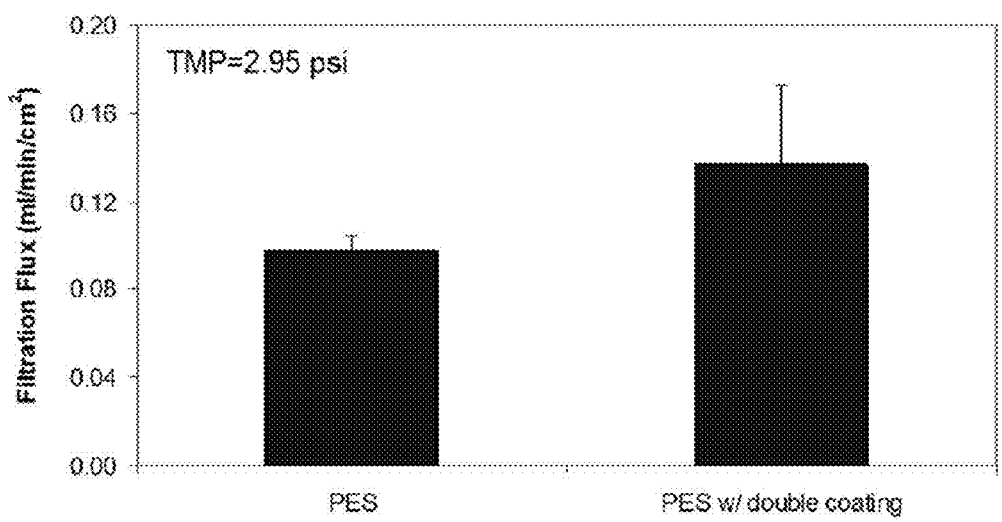
Fig. 13
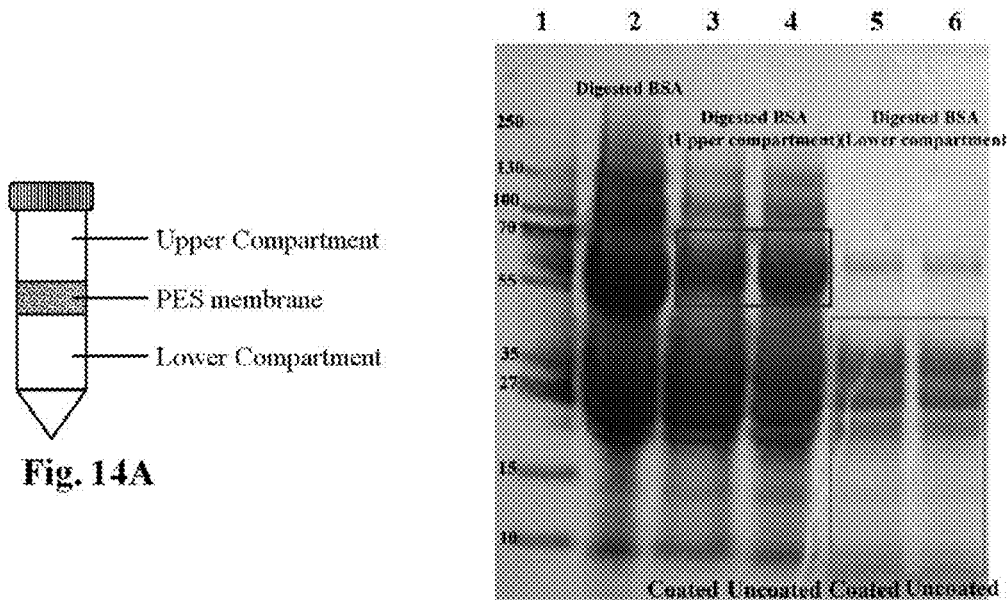
Fig. 14A
Fig. 14B

DOUBLE COATING PROCEDURE FOR THE MEMBRANES OF BIOARTIFICIAL KIDNEYS

FIELD OF INVENTION

The present invention generally relates to modified substrates such as membranes for use in bioartificial organs, such as bioartificial kidneys, and other applications.

BACKGROUND

Subjects with acute renal failure (ARF), chronic kidney disease (CKD), or end stage renal disease (ESRD) may experience moderate to severe malfunction of the nephron, the smallest functional unit of the kidney. For example, in CKD, the nephrons may still be partially functional, but as the disease progresses this function declines, and if the glomerular filtration rate is less than 10% of normal levels, the disease has progressed to ESRD. Critically ill subjects with ARF may have relatively high mortality rates, for example, between about 50% and about 70% for subjects admitted to hospitals. In addition, ARF subjects are typically dependent on hemodialysis or hemo filtration for survival.

The glomerulus is an important component of the kidney, and the structure of the glomerulus determines its permselectivity, where large and/or negatively charged molecules are prevented from passing across the glomerulus, unlike small and/or positively charged molecules. Such properties enable uremic substances, such as creatinine and urea, together with water, glucose, and ions to permeate across the glomerulus as an ultrafiltrate, and at the same time allow for the retention of blood cells and larger proteins within the circulatory system. The ultrafiltrate that is produced flows across the tubule of the nephron, whereby biological reabsorption of certain molecules back into the circulatory system occurs. The selective biological reabsorption of water, glucose, and ions is performed by an epithelium cell layer that lines the tubules. In addition, the epithelium of the proximal tubule secretes xenobiotics and drugs into the glomerular filtrate, which often cannot be efficiently cleared by glomerular filtration. Furthermore, the epithelium of the proximal tubule can help to control the pH of blood by resorption of bicarbonate. The epithelium also has important metabolic and endocrinologic functions. Molecules that are not reabsorbed are removed from the body as urine. Failure of the mechanical filtration or tubular functions, provided by the glomerulus or tubules respectively, could result in clinical complications, such as ARF, CKD, or ESRD.

With prolonged life expectancy, the ratio of subjects with CKD or ESRD that requires organ replacement to the number of suitable donors has increased. To enhance the survival rate of these subjects, hemodialysis treatment has been employed to artificially replace the mechanical filtration function of glomerulus. Polymeric membranes with open interconnected pores, in the form of hollow fibers, are often used in these dialyzers where they function as a sieving medium with carefully controlled pore sizes. This treatment is generally administered to subjects 3 or 4 times a week for 2 to 4 hours of treatment. Although successful, prolonged intermittent treatment may be detrimental over the long term due to hemodynamic instability as a result of large shift of solutes and fluids over a short period of time. In addition, it does not replace the lost reabsorption, metabolic, secretory, or endocrine functions of the tubules. Dialyzers used for hemodialysis therefore replace kidney function only incompletely, and are thus not an ideal treatment for subjects with ARF, CKD, or ESRD.

Recently, investigators have combined cellular functions within such mechanical devices to create bioartificial kidneys (BAKs). For example, bioartificial kidneys containing functional kidney cells have been developed to provide the cellular functions of tubules. BAK treatments may decrease the mortality rates of critically ill subjects having ARF. BAKs typically contain a synthetic hemo filter connected in series with a bioreactor cartridge containing porous membranes, onto which cells such as renal proximal tubule cells are seeded. Within the dialyzers conventionally used for BAKs are typically thousands of hollow fiber membranes arranged in parallel. These membranes are usually fabricated from polysulfone (PS) or polyethersulfone (PES), a PS variant that is low in protein retention. In typical BAK systems, cells such as primary human kidney proximal tubule cells (HPTCs) adhere, proliferate, and function on the polymeric membranes, which now also play the part of a cellular scaffold. However, HPTCs cultivated on these substrates have typically produced mixed results.

Primary human renal proximal tubule cells (HPTCs) have been used for clinical applications of BAKs. Such tubule cells form a simple epithelium in vivo, and perform a variety of transport, metabolic, endocrinologic, and probably also immunomodulatory functions. Transport functions of such cells include the reabsorption of glucose, small solutes, and bicarbonate from the glomerular filtrate, as well as the transport of toxins, xenobiotics, and drugs into the tubular lumen. In order to perform such functions efficiently in a BAK, however, the HPTCs must form a well-differentiated epithelium with a controllable degree of leakiness on the porous membranes. It can be difficult to seed HPTCs on suitable membrane surfaces for use in BAK systems, and/or to cause such HPTCs to form a suitable differentiated structure.

In addition and more generally, applications involving or requiring growth and differentiation of cells adhered on solid surfaces, for example in the context of bioimplants and bioartificial organs, often require expensive or difficult to manufacture materials for cell immobilization to facilitate both growth/maintenance and cell differentiation, if growth and differentiation is achievable at all. The inability of many solid materials conventionally used in and readily available for medical applications to support the growth and differentiation of certain cells seeded thereon and the difficulty of certain conventional surface modification and coating techniques in overcoming this shortcoming has been a problem in field of bioartificial organ/bioimplant design and in other fields/applications where the differentiation of cells immobilized on an artificial and/or manufactured surface is desirable.

Accordingly, improvements in such techniques are needed.

SUMMARY OF THE INVENTION

The present invention generally relates to substrates such as membranes for use in bioartificial kidneys and other applications involving immobilization of viable cells on the substrates. The subject matter of the present invention involves, in some cases, interrelated products, alternative solutions to a particular problem, and/or a plurality of different uses of one or more systems and/or articles.

In one aspect, the present invention is directed to an article. According to one set of embodiments, the article includes a substrate, an adhesive positioned on at least a portion of the substrate, a cell support protein positioned on at least a portion of the adhesive, and cells positioned on at least a portion of the substrate that is coated with the cell support protein. In some instances, the adhesive comprises a molecule having a catechol moiety and/or a polymer comprising the molecule.

In some aspects, the present invention is generally directed to a bioartificial organ. In one set of embodiments, the bioartificial organ comprises a substrate positioned to be fluidly communicable with a source of blood, an adhesive positioned on at least a portion of the substrate, a protein and/or a peptide positioned on at least a portion of the adhesive, and cells positioned on at least a portion of the protein and/or peptide. In some instances, the adhesive comprises a molecule having a catechol moiety and/or a polymer comprising the molecule.

Other aspects of the present invention are generally directed to certain methods. In accordance with one set of embodiments, the method includes acts of coating at least a portion of a substrate with an adhesive comprising a molecule having a catechol moiety and/or a polymer comprising the molecule, coating at least a portion of the adhesive with a cell support protein, and seeding cells on at least a portion of the cell support protein. The method, in certain instances, includes acts of coating at least a portion of a substrate with an adhesive, coating at least a portion of the adhesive with a protein, and seeding cells on at least a portion of the substrate that is coated with the protein. In some embodiments, the protein may facilitate differentiation of the cells seeded on the substrate.

In another aspect, the present invention encompasses methods of making one or more of the embodiments described herein, for example, a coated membrane. In still another aspect, the present invention encompasses methods of using one or more of the embodiments described herein, for example, a coated membrane.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 1 illustrates an example of a bioartificial kidney, in accordance with certain embodiments of the invention.

FIGS. 2A-2F are photomicrographs that illustrate human renal proximal tubule cells on different polymer membranes, in accordance with certain embodiments of the invention;

FIGS. 12A-12D are photomicrographs that illustrate human renal proximal tubule cell growth on certain membranes, in accordance with various embodiments of the invention;

FIG. 13 is a graph that illustrates water flux through coated and uncoated membranes, in accordance with certain embodiments of the invention;

FIG. 14A is a photographic image that illustrates an ultrafiltration spin column sold under the trademark Vivaspin™;

FIG. 14B is a photographic image of a gel that illustrates the permeability of certain membranes for protein fragments, in accordance with one embodiment of the invention.

DETAILED DESCRIPTION

Figure 3:
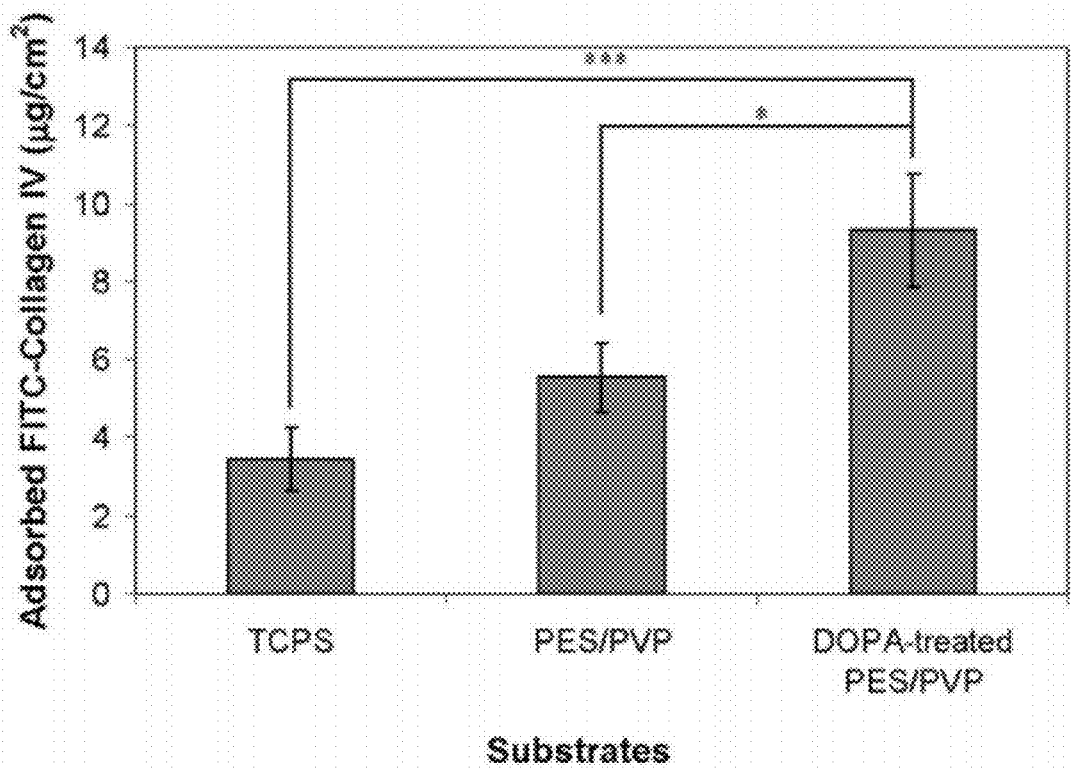
FIG. 3 is a graph that illustrates the adsorption of FITC-conjugated collagen type IV on different substrates, in some embodiments of the invention.

The present invention generally relates to modified substrates such as membranes for use in bioartificial organs, such as bioartificial kidneys, and other applications. Certain aspects are generally directed to a membrane or other substrate modified to facilitate the attachment of cells. In one set of embodiments, the substrate or membrane may be at least partially coated with an adhesive such as 3,4-dihydroxy-L-phenylalanine (DOPA), 3,4-dihydroxy-D-phenylalanine, poly(dopamine), poly(DOPA), poly(3,4-dihydroxy-D-phenylalanine), or other adhesive comprising a molecule having a catechol moiety, for example on one side of the membrane or substrate. On at least a portion of the adhesive coated portion of the substrate, a protein may be coated, such as an extracellular matrix protein (for example, a collagen), to which cells such as primary human renal proximal tubule cells may be adhered. Surprisingly, such a dual coating may be used to promote the attachment of such cells to a membrane or other substrate that otherwise may not promote cell adhesion. In certain embodiments, the coating may also facilitate or promote not only cell adhesion, but also cell proliferation and/or differentiation. Such membranes or other substrates may be useful, for example, in bioartificial organs such as bioartificial kidneys, hemodialysis cartridges, bioimplants, biosensors, bioreactors, etc. In certain embodiments, cells may be attached to a membrane or other substrate on only one side, while the other side may be kept free of attached cells.

Membranes or substrates provided according to certain embodiments of the invention may be used in applications such as bio artificial organ devices, where blood is withdrawn from a subject and passed into/through the device. Thus, for example, the membrane or other substrate can be positioned within the device to be fluidly communicable with a source of blood, e.g., of a subject such as a human or non-human animal. The substrate/membrane may be treated such that a first portion of the substrate/membrane is substantially free of cells while a second portion of the substrate/membrane contains attached cells. In one set of embodiments, these regions may be on opposite sides of the substrate or membrane, e.g., such that the substrate or membrane separates one chamber exposed to blood from another chamber containing attached cells that are able to interact with the blood, or portions thereof able to pass across the membrane. For example, the membrane can be an ultrafiltration membrane, a hemodialysis membrane, a hemo filtration membrane, and/or a semi-permeable membrane, e.g., as discussed below, where one or more components of blood are able to pass from a first chamber, across the membrane, to a second chamber, while cells such as blood cells and other components from the blood (e.g., serum proteins or fibrin) are not able to substantially attach to the region of the membrane that is directly exposed to the blood. In contrast, in the second chamber, there may be one or more cells or cell types attached to the membrane which can interact with the components of blood transported across the membrane, e.g., to purify the blood, to cause a chemical reaction to occur, to add or remove material from the blood, or the like. As a specific, non-limiting example, in the case of a bio artificial kidney, the cells may be used to transport water, glucose, proteins, and/or small solutes from the ultrafiltrate, to which they are exposed, into the blood, and/or the cells may be allowed to produce or secrete other substances, such as 1,25-dihydroxy vitamin $D_3$ (produced by the cells), into the blood As a specific example, the bioartificial organ may be a bioartificial kidney or a hemodialysis cartridge used for dialysis. Non-limiting examples of bioartificial kidneys are discussed below with reference to FIG. 1. Many types of hemodialysis cartridges are readily available commercially. Membranes may be used in such devices to separate a first chamber containing blood withdrawn from a subject from a second chamber containing cells able to interact with components of the blood transported across the membrane. The second chamber may also contain an ultrafiltrate, from which the cells are able to reabsorb substances. However, the cells within the second chamber may not be able to escape to enter the blood of the subject, e.g., due to the presence of the substrate or membrane.

Typically, a bioartificial kidney contains two (or more) units, for example, two cartridges such as hemodialysis or hemofiltration cartridges. The first unit may be used to perform normal hemofiltration, e.g., where an ultrafiltrate containing uremic toxins is separated from the blood. The first unit may not contain any immobilized renal cells. The ultrafiltrate and the blood can then flow into the second unit, which may contain cells such as those described herein. The ultrafiltrate is in the same chamber where the cells are (e.g., in the lumen of hollow fiber membranes), while the blood is in a different chamber (e.g., outside of the hollow fiber membranes). The cells in the second unit may be able to exchange substances between the bloodstream and the ultrafiltrate, e.g., as discussed herein. Non-limiting examples of bioartificial kidneys can be seen in International Patent Application No. PCT/SG2010/000380, filed Oct. 6, 2010, titled "Delivery of BMP-7 and Methods of Use Thereof," by Zink, et al.; and International Patent Application No. PCT/SG2010/000377, filed Oct. 4, 2010, titled "Improved Bioartificial Kidneys," by Ying, et al., each incorporated herein by reference. As another example, hepatocytes may act to detoxify substances from the blood, or interact with proteins, amino acids, carbohydrates, etc. found in the blood. As yet another example, pancreatic beta-cells may be used to produce insulin in response to blood glucose levels within the blood of a subject. It may be desired to have such cells be able to interact with blood removed from the subject, e.g., for treatment or therapeutic purposes, while reducing or eliminating the ability of such cells to enter the blood and/or body of the subject (e.g., when the blood is returned to the subject).

The membrane or other substrate modifiable according to the invention can be formed from any suitable material, e.g., a polymer or plastic, glass, ceramic, a metal, etc., as well as combinations of these and/or other materials. In some embodiments, the substrate or membrane may contain one or more holes, pores, channels, pathways, etc., which can allow filtration or transport of components from blood, while at the same time preventing access or transport of cells through the substrate or membrane. For example, a membrane may be a semi-permeable membrane, e.g., a membrane that will allow only certain molecules and/or ions to pass through it by diffusion and/or convection, and/or an ultrafiltration membrane, e.g., having an average pore size of less than about 1 micrometer, less than about 500 nm, less than about 300 nm, less than about 100 nm, less than about 50 nm, less than about 30 nm, less than about 10 nm, less than about 5 nm, less than about 3 nm, etc. Such pore sizes may be determined, for example, using BET or mercury porosimetry, or estimated using electron microscopy.

In some embodiments, the membrane or substrate may have a pore size that can be used to control selectivity, e.g., of a protein. For example, the membranes can have a total protein permeability (e.g., of proteins typically found within the blood) of less than about 10%, less than about 5%, less than about 2%, less than about 1%, less than about 0.5%, less than about 0.2%, less than about 0.1%, etc. In some cases, the pore size of the membrane may be chosen such that the membrane may have a predetermined molecular weight cut-off (MWCO) value. For instance, the membrane may have a MWCO of less than about 50,000 Da, less than about 30,000 Da, less than about 20,000 Da, less than about 10,000 Da, less than about 5,000 Da, less than about 2,000 Da, less than about 1,000 Da, etc. (As is understood by those of ordinary skill in the art, MWCO is commonly used as a guide or estimate as to the pore size, rather than as a strict numerical limitation.) As a specific non-limiting example, in some embodiments, the membrane is able to remove uremic substances (e.g., urea and creatinine) from blood selectively, while preventing leakage of useful proteins (e.g., albumin).

In some embodiments, the membrane or other substrate is formed from or comprises a polymer. The polymer may be any suitable polymer for use in applications where a membrane or other substrate is intended to interact with blood, and in some cases, is used to separate cells from blood, e.g., from a source of blood such as a human subject. The polymer may be, for example, polysulfone (PSF), polyethersulfone (PES), polyvinylpyrrolidone (PVP), and/or any combination of these and/or other polymers, e.g., PES/PVP and PSF/PVP and co-polymers of any of the polymers mentioned herein. As yet another example, an acrylic-based photopolymer such as Fullcure™ (Objet Geometries, Inc.) may be used. As still another example, the polymer may be regenerated cellulose. Additional examples of polymers that can be used to form structures described herein include, but are not limited to, cellulose acetate, polyarylethersulfone, polyvinyl alcohol, polyvinylbutryl, polyvinylpyridyl, polyvinyl pyrrolidone, polyvinyl acetate, polyacrylonitrile, acrylonitrile butadiene styrene (ABS), ethylene-propylene rubbers (EPDM or EPR), chlorinated polyethylene (CPE), ethelynebisacrylamide (EBA), acrylates (e.g., alkyl acrylates, glycol acrylates, polyglycol acrylates, ethylene ethyl acrylate (EEA)), hydrogenated nitrile butadiene rubber (HNBR), natural rubber, nitrile butadiene rubber (NBR), certain fluoropolymers, silicone rubber, polyisoprene, ethylene vinyl acetate (EVA), chlorosulfonyl rubber, flourinated poly(arylene ether) (FPAE), polyether ketones, polysulfones, polyether imides, diepoxides, diisocyanates, diisothiocyanates, formaldehyde resins, amino resins, plyurethanes, unsaturated polyethers, polyglycol vinyl ethers, polyglycol divinylethers, poly(anhydrides), polyorthoesters, polyphosphazenes, polybutylenes, polycapralactones, polycarbonates, and protein polymers such as albumin, collagen, and polysaccharides, copolymers thereof, and monomers of such polymers.

Still other examples of polymers that can be used to form membranes or other substrates as described herein include but are not limited to, polyamines (e.g., poly(ethylene imine) and polypropylene imine (PPI)); polyamides (e.g., polyamide (Nylon), poly(e-caprolactam) (Nylon 6), poly(hexamethylene adipamide) (Nylon 66)), polyimides (e.g., polyimide, polynitrile, and poly(pyromellitimide-1,4-diphenyl ether) (Kapton)); vinyl polymers (e.g., polyacrylamide, poly(2-vinyl pyridine), polyvinylpyrrolidone), poly(methylcyanoacrylate), poly(ethylcyanoacry late), poly(butylcyanoacrylate), poly(isobutylcyanoacrylate), poly(vinyl acetate), poly(vinyl alcohol), poly(vinyl chloride), poly(vinyl fluoride), poly(2-vinyl pyridine), vinyl polymer, polychlorotrifluoroethylene, and poly(isohexylcynaoacrylate)); polyacetals; polyolefins (e.g., poly(butene-1), poly(n-pentene-2), polypropylene, polytetrafluoroethylene); polyesters (e.g., polycarbonate, polybutylene terephthalate, polyhydroxybutyrate); poly ethers (poly(ethylene oxide) (PEO), poly(propylene oxide) (PPO), poly(tetramethylene oxide) (PTMO)); vinylidene polymers (e.g., polyisobutylene, poly(methyl styrene), poly(methylmethacrylate) (PMMA), poly(vinylidene chloride), and poly(vinylidene fluoride)); polyaramides (e.g., poly(imino-1,3-phenylene iminoisophthaloyl) and poly(imino-1,4-phenylene iminoterephthaloyl)); polyheteroaromatic compounds (e.g., polybenzimidazole (PBI), polybenzobisoxazole (PBO) and polybenzobisthiazole (PBT)); polyheterocyclic compounds (e.g., polypyrrole); polyurethanes; phenolic polymers (e.g., phenol-formaldehyde); polyalkynes (e.g., poly acetylene); polydienes (e.g., 1,2-polybutadiene, cis- or trans-1,4-polybutadiene); polysiloxanes (e.g., poly(dimethylsiloxane) (PDMS), poly(diethylsiloxane) (PDES), poly(tetrafluoroethylene) (PTFE), poly(ethylene) (PE), a polyolefin, polydiphenylsiloxane (PDPS), and polymethylphenylsiloxane (PMPS)); and inorganic polymers (e.g., polyphosphazene, polyphosphonate, polysilanes, polysilazanes). Additional polymers that may be used are described in International Patent Application Serial No. PCT/US2006/035610, titled, "Porous Polymeric Articles," by Ying et al., filed on Sep. 12, 2006, published as WO 2008/005035 on Jan. 10, 2008, which is incorporated herein by reference. In some embodiments, commercially available membranes, such as Pall Omega™ membranes (Pall Corporation), may be used.

Other materials may be used in the substrate, instead of or in addition to a polymer. For example, the substrate may comprise glass, a metal, a ceramic, a semiconductor, or the like.

In some embodiments, the membrane or other substrate may be treated with or comprise one or more compositions that impart anti-fouling properties to the membrane or substrate. For example, the membrane or other substrate may comprise 2-methacryloyloxyethyl phosphorylcho line, 3-methylacryloyloxy propyltrimethoxysilane, or other non-fouling compositions.

In some embodiments, the membrane or other substrate may be selected to yield desired performance properties. For example, decreasing the membrane thickness may allow more efficient ultrafiltration by shortening the distance that fluid must flow from one side to the other. The thickness of the membrane can be, in some embodiments, between 50 micrometers and 500 micrometers, between 50 micrometers and 400 micrometers, between 50 micrometers and 300 micrometers, between 50 micrometers and 200 micrometers, between 100 micrometers and 500 micrometers, between 100 micrometers and 400 micrometers, or between 200 micrometers and 400 micrometers.

However, decreasing the thickness also may decrease the mechanical strength of the membrane or substrate. Accordingly, in some embodiments, a macroporous support layer may be used to strengthen the membrane or other substrate. For example, a support layer may be placed adjacent to a membrane or other substrate in a bioartificial kidney (or other bioartificial organ), e.g., in fluid communication with a source of ultrafiltrate or hemofiltrate. Any suitable biocompatible material may be used to fabricate the support layer. In some embodiments, the support layer may be macroporous relative to the membrane or other support. Non-limiting examples of polymers that may be used to fabricate the support layer include the polymers described above. The support layer and the membrane or substrate may also be formed out of the same or different materials.

The membrane or substrate may have any suitable shape and configuration. For example, the membrane may have a tubular configuration e.g., as in a hollow-fiber dialysis cartridge or a hemodialysis cartridge, or a non-tubular configuration. In some embodiments, the membrane may be in the form of a substantially flat sheet. For example, the membrane may be disk- or plate-like, with a thickness substantially less than a width, length, or diameter of the membrane).

In certain aspects, cells may be incorporated into devices incorporating the membranes or substrates of the invention. However, within such devices, the membrane or other substrate used to separate the blood from the cells typically advantageously simultaneously promotes the adhesion of cells on the cellular side (e.g., of cells such as kidney cells or hepatocytes) while reducing or inhibiting the adhesion of cells on the blood side (e.g., of cells such as platelets or macrophages). One method of providing such functionality is to use a membrane or other substrate having different properties on different sides. For example, one side can be relatively cytophobic while the other side is relatively cytophilic. Accordingly, in one set of embodiments, a relatively cytophobic membrane and/or a hemocompatible membrane, or other substrate is used in which one side of the membrane is treated to render it relatively cytophilic. Examples of hemocompatible membranes include those commercially available for use in hemodialysis; these membranes often exhibit reduced adhesion of cells and blood protein such as serum albumin and fibrin. For example, as discussed below, one side of the membrane or other substrate may be coated with a cell support protein, optionally via an adhesive to facilitate binding of with the cell support protein to the membrane.

In some embodiments, there may be one or more proteins adhered to the membrane or other substrate. For example, the membrane or other substrate can include one or more cell support proteins. The "cell support protein" may be any protein or peptide that at least facilitates adhesion, and may also promote growth and/or differentiation of cells that are attached or in contact with the protein. For instance, there can be a greater number of relevant cells (e.g., human renal proximal tubule cells for a bioartificial kidney) attached to a membrane or other substrate, and optionally form a polarized epithelium, when the cell support protein is present than when it is not present. The cell support protein may be natural or man-made, and may be human or human-derived, derived from another organism (e.g., a murine protein), or one that is artificially created. The cell support protein may be obtained from any suitable source, e.g., synthesized, grown in vitro in cells, acquired from certain organisms, etc. It should be noted that, as used herein, the terms "protein" and "peptide" are interchangeable, i.e., there is no specific agreed-upon cut-off in terms of length or number of residues between a protein and a peptide, as is understood by those of ordinary skill in the art. Examples of cell support proteins include, for example, extracellular matrix protein and/or polycationic peptides.

In some embodiments, at least about 50% of the protein on the membrane or other substrate, or at least on one surface thereof, is a cell support protein such as an extracellular matrix protein, and in certain cases, at least about 60%, at least about 70%, at least about 80%, at least about 90%, at least about 95%, or at least about 99% of the protein on the membrane or other substrate is a cell support protein. In some cases, at least a portion of the cell support protein may include one or more extracellular matrix proteins, and in certain embodiments, at least about 50%, at least about 60%, at least about 70%, at least about 80%, at least about 90%, at least about 95%, or at least about 99% of the cell support protein on a membrane or other substrate comprises one or more extracellular matrix proteins.

A wide variety of cell support proteins can be used. The cell support protein may be a protein that improves cell differentiation, cell adhesion, cell spreading, cell migration, or the like. Non-limiting examples of suitable extracellular matrix proteins useful or potentially useful as a cell support protein include laminin, fibronectin, vitronectin, elastin, tenascin, or various collagens (e.g., collagen type I, collagen type II, collagen type III, collagen type IV, collagen type V, collagen type VI, collagen type VII, collagen type VIII, collagen type IX, collagen type X, collagen type XI, collagen type XII, collagen type XIII, collagen type XIV, collagen type XV, collagen type XVI, collagen type XVII, collagen type XVIII, collagen type XIX, collagen type XX, collagen type XXI, collagen type XXII, collagen type XXIII, collagen type XXIV, collagen type XXV, collagen type XXVI, collagen type XXVII, collagen type XXVIII, or collagen type XXIX). The collagen may come from any suitable source, e.g., human placental collagen, dermal collagen, etc. Examples of polycationic peptides suitable or potentially suitable for use as a cell support protein include, but are not limited to, poly-L-lysine, poly-L-arginine, poly-L-histidine, and/or copolymers or blends of these and/or other suitable polycationic peptides or other species. Still other examples of cell support proteins include proteins comprising an RGD sequence (arginine-glycine-aspartic acid), which is a sequence commonly found in extracellular matrix proteins such as those described above. Such sequences may be derived from or otherwise be found in certain extracellular matrix proteins, thus, the sequence may be one characteristic of an extracellular matrix protein. As yet another example, the cell support protein may be a synthetic peptide comprising a sequence characteristic of an extracellular matrix protein, for example, an RGD sequence. In some cases, the cell support protein may facilitate cell differentiation of cells on the substrate or membrane. One non-limiting example of such a protein is bone morphogenic protein 7 (BMP-7). See, e.g., International Patent Application No. PCT/SG2010/000380, filed Oct. 6, 2010, titled "Delivery of BMP-7 and Methods of Use Thereof," by Zink, et al., incorporated herein by reference.

In some aspects, a protein such as an extracellular matrix protein may be adhered to or otherwise immobilized relative to the membrane or other substrate using an adhesive. The adhesive may be positioned between the protein and the membrane or other substrate, and may cause or enhance adhesion of the protein with respect to the membrane or other substrate via any suitable mechanism (depending on the nature of the protein, the adhesive and the membrane/substrate), e.g., covalent bonding, noncovalent bonding, ionic forces, van der Waals interactions, hydrogen bonding, physical intercalation or the like. The adhesive may be any suitable material able to increase the amount or concentration of protein adhered to or immobilized to the membrane or other substrate, relative to the amount or concentration of protein able to be adhered in the absence of the adhesive. In some embodiments, the adhesive is positioned on only one side of the membrane or other substrate.

In one set of embodiments, the adhesive comprises a molecule having a catechol moiety, e.g., a moiety such as:

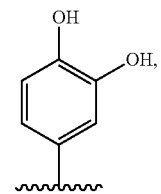 [SMILES: *c1ccc(O)c(O)c1]

where the wavy line indicates the point of attachment of this moiety to the rest of the molecule, e.g., as shown in the examples below that include a catechol moiety. Thus, non-limiting examples of such adhesives include 3,4-dihydroxy-L-phenylalanine (DOPA) and 3,4-dihydroxy-L-phenylalanine-lysine. In some cases, the adhesive is or includes a polymer or copolymer comprising a catechol moiety, such as poly(dopamine), poly(dopamine methacrylamide-co-methoxyethyl acrylate) (pDMA-co-MEA), PEG-DOPA, etc. DOPA has the following structure:

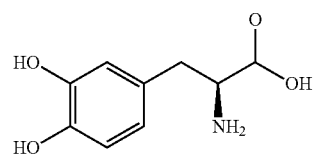 [SMILES: N[C@@H](Cc1ccc(O)c(O)c1)C(O)O]

pDMA-co-MEA has the following structure:

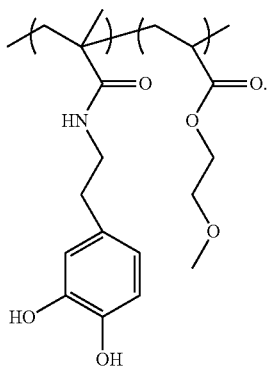

In addition, in other embodiments, combinations of these and/or other adhesives, e.g., other adhesives comprising molecules having catechol moieties, may be used.

Without wishing to be bound by any theory, it is believed that adhesives comprising molecules including a catecholic amino acid may be able to participate in certain cross-linking reactions leading to solidification of certain proteins, for which there may be a role for metal ions such as $Fe^{3+}$ in the cross-linking reaction. Thus, in some cases, oxidized catecholic amino acid residues may play a role in cross-linking reactions leading to solidification of the adhesive. In addition, aside from cross-linking, DOPA is known to have high affinity for a variety of chemically distinct surfaces: organic and inorganic, via coordination, covalent bonds, hydrogen bonds, etc. Also, in some embodiments, adhesives such as DOPA may coat and/or convert and/or react with the surface of the substrate to transform it into a form that is more cytophilic, even in certain cases in the absence of a cell support protein. For example, a substrate treated with DOPA or other such adhesives, followed by treatment with a cell support protein, may exhibit better cell adhesion properties than a similar surface treated with the cell support protein but in the absence of DOPA or other adhesive.

Thus, in various embodiments of the invention, one or more cells and/or cell types may be positioned on a cell support protein positioned on the membrane or other substrate, e.g., by being attached or adhered thereto via an adhesive. The surface can be partially or completely covered with cells. Any suitable cells may be used, depending on the application. For example, the cells may include human and/or non-human cells, e.g., non-human mammalian cells. Specific non-limiting examples of cells include kidney cells (e.g., renal proximal tubule cells), liver cells (e.g., hepatocytes), lymphocytes, pancreatic beta-cells (e.g., for producing insulin for delivery into the blood), lymph cells, or the like. As additional non-limiting examples, the cells may include or consist essentially of primary cells, non-immortalized cells, stem cells (e.g., embryonic, mesenchymal and induced pluripotent (iPS) stem cells), differentiated cells (e.g., obtained from stem cells), etc.

As a specific non-limiting example, the cells on the membrane or other substrate can comprise renal proximal tubule cells, for example, for applications such as bioartificial kidneys, which may include one or more hemodialysis cartridges containing such cells. In some cases, as discussed herein, the cells are positioned only on one surface of the membrane or other substrate, e.g., on a side that is isolated from the blood side of the device. In certain embodiments, the cells may form a continuous layer on at least a portion the membrane such that ultrafiltrate cannot pass through the membrane without passing through the renal proximal tubule cell layer. For example, in some embodiments, the cells form a confluent epithelium on the membrane. In certain embodiments, the paracellular spaces may be sealed by tight junctions. In some cases, the cells are able to form a monolayer on the surface of the membrane.

In one set of embodiments, the renal proximal tubule cells are co-cultured with other cells. For example, in certain embodiments, the renal proximal tubule cells may be co-cultured with renal cell types (e.g. distal tubule cells, collecting duct cells, podocytes and renal fibroblasts) or endothelial cells. In some embodiments, the performance of renal proximal tubule cells (e.g., the ability to reabsorb substances) may be improved in co-cultures.

In some embodiments, one or more agents can be used to promote formation and/or maintenance of renal proximal tubule cell morphology and confluence, for instance, as discussed in International Patent Application No. PCT/SG2010/000380, filed Oct. 6, 2010, titled "Delivery of BMP-7 and Methods of Use Thereof," by Zink, et al., incorporated herein by reference. For example, in some embodiments, bone morphogenic protein 7 (BMP-7) may be used as an agent. In some embodiments, one or more agents may be released in controlled fashion from within the BAK. In some cases, one or more agents may be produced within the renal tubule cells.

In addition, some aspects of the present invention are directed to systems and methods for producing polymer membranes such as those described herein. For example, a polymer membrane or other substrate can be coated with an adhesive, such as an adhesive comprising molecules having a catechol moiety. The membrane or other substrate, or a portion thereof, may be first exposed to a solution containing such an adhesive, or a precursor of the adhesive. For example, the membrane or substrate may be dipped in a solution, the solution may be brushed on, or the solution may be added to the membrane or substrate using spin-coating techniques. The solution may optionally then be allowed to dry (e.g., via waiting, heating, exposure to a dry environment, etc.), and optionally, polymerization may be induced within the drying solution, e.g., through free radical copolymerization of DMA and MEA monomers to form p(DMA-co-MEA), although in certain applications the membrane may only be washed (e.g. with deionized water) but not dried.

Once sufficient drying has occurred, the adhesive may be coated with another solution containing one or more cell support proteins, e.g., an extracellular matrix protein or other protein(s) as discussed herein. Coating with protein may be performed, e.g., using techniques such as those described above. The coating process may be the same or different from the coating process used with the adhesive. The coating may also be dried, e.g., using techniques such as those described above. The adhesive may promote adhesion of the cell support proteins to the substrate. However, in some embodiments, some cell support proteins may be able to adhere to the membrane or other substrate, at least partially, without the presence of the adhesive in those regions.

Once sufficiently dried or washed, one or more cells or cell types may be seeded or plated on the membrane or other substrate, e.g., on at least a portion of the membrane/substrate coated with cell support protein. Any suitable technique for seeding cells on a substrate can be used, e.g., by applying a solution containing the cells to the substrate, e.g., on the portion of the substrate where the cell support protein is located. In some cases, other portions of the membrane or substrate may be seeded as well.

In addition, certain aspects of the present invention are generally directed to bioartifical kidneys or BAKs. Non-limiting examples of bioartificial kidneys may be found in International Patent Application No. PCT/SG2010/000377, filed Oct. 4, 2010, titled "Improved Bioartificial Kidneys," by Ying, et al., incorporated herein by reference in its entirety. In some embodiments, the BAKs may comprise an ultrafiltration unit and a bioreactor unit (e.g., containing immobilized cells). In some embodiments, the ultrafiltration unit and the bioreactor unit may be contained in a single housing, which may be partitioned, in certain cases, into a first rigid walled compartment containing the ultrafiltration unit and a second rigid walled compartment containing the bioreactor unit. In certain other embodiments, the single housing, which may contain only a single rigid walled compartment containing both membrane(s) forming an ultrafiltration section (ultrafiltration unit) and membrane(s) forming a bioreactor unit. In certain embodiments, the ultrafiltration unit and the bioreactor unit are each contained in a physically separate, independently movable housing, where the housings are connected in fluid communication with each other.

The bioreactor unit generally contains a reabsorption membrane, at least a portion of which may have a plurality of renal proximal tubule cells disposed thereon, where the renal proximal tubule cells selectively transport molecules and selectively allow solutes to pass through the reabsorption membrane. In certain embodiments, the plurality of human renal proximal tubule cells forms substantially a monolayer of cells on at least a portion of the membrane of the bioreactor unit, and in certain such embodiments the plurality of human renal proximal tubule cells forms substantially a monolayer of cells on substantially the entirety of at least one side of the membrane of the bioreactor unit. In some embodiments, the bioreactor unit may be configured as a substantially flat device (e.g. disk- or plate-like with a thickness substantially less than a width, length, or diameter of the device), which can impart advantageous properties such as improved maintenance of the renal proximal tubule cell layer and more facile monitoring of the renal proximal tubule cell layer, as well as, in certain embodiments, greater portability and wearability. In other embodiments, the resorption unit comprises a hollow-fiber filtration or dialysis cartridge.

A non-limiting example of a hollow fiber BAK is shown in FIG. 1. BAK 100 comprises an inlet 110 that is in fluid communication with the circulation system 111 of a subject. Blood flows into the filtration unit 120 through the inlet. The filtration unit comprises a plurality of hollow fiber membranes 121 through which fluid, but not cells, can pass. "Ultrafiltrate" refers to the fluid that has been passed through the membrane. "Retentate" refers to the portion of the blood that does not cross the membrane. The blood flows into the hollow fibers of the filtration unit and fluid from the blood passes through the hollow fiber membranes resulting in formation of an ultrafiltrate in the spaces 122 exterior to the hollow fibers. The retentate 123 and ultrafiltrate 124 then flow into the bioreactor unit 130. The bioreactor unit comprises hollow fiber membranes 131 into which the ultrafiltrate from the filtration unit flows. The retentate from the filtration unit flows into the spaces 132 exterior to the hollow fibers. The interior surface of the hollow fibers of the bioreactor unit has renal proximal tubule cells 133 seeded thereon. The ultrafiltrate from the filtration unit flows into hollow fibers of the bioreactor unit where it contacts the renal proximal tubule cells. A portion of the fluid from the ultrafiltrate passes through the hollow fibers seeded with renal proximal tubule cells into the spaces exterior to the hollow fibers. This fluid is herein referred to as the "reabsorbate." Like the tubules of the kidney, the human proximal tubule cells may perform their biological functions in regulating the reabsorption and metabolism of important substances such as glucose, water, and ions. In some non-limiting embodiments, a therapeutically active protein or other agent may be released by the cells and/or another component in the bioreactor unit (e.g. exemplified in FIG. 1 by BMP-7 140). The residual ultrafiltrate 135 flows out of the BAK and into a waste container. In some embodiments, the combined retentate and reabsorbate 136, flows out of the BAK and back into the circulation system of a subject. In some embodiments, a flat-bed BAK may be used, for example, as described in International Patent Application No. PCT/SG2010/000377, filed Oct. 4, 2010, titled "Improved Bioartificial Kidneys," by Ying, et al., which is incorporated herein by reference.

The following documents are incorporated herein by reference: International Patent Application No. PCT/SG2010/000380, filed Oct. 6, 2010, titled "Delivery of BMP-7 and Methods of Use Thereof," by Zink, et al.; and International Patent Application No. PCT/SG2010/000377, filed Oct. 4, 2010, titled "Improved Bioartificial Kidneys," by Ying, et al.

The following examples are intended to illustrate certain embodiments of the present invention, but do not exemplify the full scope of the invention.

Example 1

Bioartificial kidneys (BAKs) combine a conventional hemo filter in series with a bioreactor containing renal cells, such as renal proximal tubule cells. The cells may provide functions like reabsorption of glucose, amino acids, bicarbonate, electrolytes and water, secretion of toxins and xenobiotics, production of 1,25-dihydroxy vitamin $D_3$, and immunomodulatory functions. Human primary renal proximal tubule cells (HPTCs) have been used in clinical trials and they are effective for BAK applications.

The proximal tubule cells are typically properly differentiated and may form confluent epithelia sealed by tight junctions on the porous membranes of the BAK. If this should not occur, the cellular functions may be compromised in some instances. Under such conditions, the entire BAK may still perform the functions of a normal hemofiltration device, but diffusion of ultrafiltrate components back into the blood in the bioreactor unit may occur.

This example investigates the performance of human renal proximal tubule cells on various polymeric membranes, which were either untreated, or subjected to different surface treatments and coating procedures.

PES (Ultrason® E6020P), with an average molecular weight (MW) of 51 kDa, was purchased from BASF (Ludwigshafen, Germany). PVP (average MW of 25 kDa) was purchased from Merck (Singapore). N-methyl-2-pyrrolidone (NMP) (Merck, Darmstadt, Germany) and N,N-dimethylacetamide (DMAc, Sigma-Aldrich, Singapore) were used as solvents. PSF (average MW of 22 kDa), poly(ether imide) (PEI, average MW of 12 kDa), poly(maleic anhydride-alt-1-octadecene) (PA-18, MW ~30-50 kDa), poly-L-lysine (PLL, 0.01%), 3,4-dihydroxy-L-phenylalanine (DOPA), and hydrogen peroxide (31%) were purchased from Sigma-Aldrich. Commercial regenerated cellulose membranes (Millicell®-HA) were purchased from Millipore (Cork, Ireland) and commercial poly(ethylene terephthalate) (PET, Transwell®) membranes were obtained from Corning (Corning, N.Y., USA).

Preparation of PES/PVP, PSF/PVP and PSF membranes and surface treatments: PES/PVP and PSF/PVP membranes were prepared by phase inversion methods. Briefly, PES and PVP were dissolved in NMP with a final composition of 18/8/74 wt % PES/PVP/NMP. About 5 ml of the polymer solution was introduced on a silicon wafer and spun at 1500 rpm for 30 sec by using a commercial spin coating apparatus (CEE 100CB Coat Bake System, Brewer Science, Rolla, Mo., USA). After spinning, the wafer was directly dipped in a water bath. After natural peeling from the silica wafer, the PES/PVP membrane was washed with a large volume of deionized (DI) water and stored in DI water at room temperature before use. Similarly, PSF/PVP and PSF membranes were prepared with a final concentration of 20/5/75 wt % PSF/PVP/NMP or 25/75 wt % PSF/NMP, respectively. All membranes were made under the same spin-coating conditions (1500 rpm, 30 sec). The conditions used for the different surface treatments are listed in Table 1.

TABLE 1

Surface treatments of PES/PVP membranes.

| Surface treatments | Chemical | Conditions |
| --- | --- | --- |
| PA-18 | poly (maleic anhydride-alt-1- octadecene) | 2 wt % in DI water, overnight |
| PLL | poly-L-lysine | 0.01 wt % in DI water, overnight |
| Hydrogen peroxide | — | 31 vol %, overnight |
| Oxygen plasma | — | 40 W, 5 min |
| DOPA | 3,4-dihydroxy-L-phenylalanine | 0.2 wt % in 10 mM of Tris buffer, pH 8.5, overnight |

Water contact angle measurements: One microliter of DI water was pipetted on a membrane surface. Water contact angles were measured with a goniometer (Contact Angle System OCA 30, DataPhysics Instruments GmbH, Filderstadt, Germany) using the SCA20 software.

Zeta potential measurements: The zeta potentials of untreated and treated PES/PVP membranes were measured by using an electro kinetic analyzer (EKA 1.00, Anton-Paar GmbH, Graz, Austria) equipped with a plated sample cell. Membranes were cut into 2 cm×1 cm pieces. The measurements were conducted at 25° C. in 1 mM of KCl solution at pH 6.8. In each case, measurements were performed with three replicas.

Characterization of carboxylic acid groups on membrane surfaces: The surface density of carboxylic acid groups on untreated and treated PES/PVP membranes was determined by using a toluidine blue O (TBO) staining assay. Membranes were immersed in 0.5 mM of TBO solution at pH 10. The non-complexed dye molecules were removed by washing with DI water. Dye molecules that were adsorbed onto the carboxylic acid groups were desorbed in a 50% acetic acid solution. The dye concentration in this solution was determined by measuring the absorbance at 633 nm using a microplate reader (Tecan Safire2™, Männedorf, Switzerland).

X-ray photoelectron spectroscopy (XPS): XPS was performed with a VG ESCA 220i-XL Imaging XPS system (LPD Lab Services, Blackburn, UK). Al Kα (K-alpha) X-rays were used as the source (hν (h nu)=1486.6 eV). All binding energies for the samples were referenced by setting the adventitious carbon C(1s) peak to 285 eV.

In vitro cell culture: HK-2 cells and one batch of HPTCs were obtained from the American Type Culture Collection (ATCC, Rockville, Md., USA). HK-2 cells were cultured with Dulbecco's modified Eagle's medium (DMEM) supplemented with 10% fetal bovine serum (FBS, Invitrogen, Carlsbad, Calif., USA). HPTCs from ATCC were cultured in renal epithelial cell basal medium supplemented with 0.5% FBS and renal epithelial cell growth kit-BBE (ATCC). Additional batches of HPTCs were obtained from ScienCell Research Laboratories (Carlsbad, Calif., USA), and cultivated in the medium recommended by the vendor, which was basal epithelial cell medium supplemented with 2% FBS and 1% epithelial cell growth supplement (ScienCell Research Laboratories). Only early-passage HPTCs (passage 3 to 5) were applied, and different batches of primary cells were used in order to exclude batch-dependent influences. All cell culture media were supplemented with 1% penicillin/streptomycin solution (Gibco, Carlsbad, Calif., USA), and all cells were propagated with standard tissue-culture plastic ware and incubated at 37° C. in a 5% $CO_2$ atmosphere. Cell counting was performed with the Vi-Cell™ analyzer (Beckman Coulter, Fullerton, Calif., USA).

Bioreactor conditions and γ (gamma)-glutamyltransferase (GGT) assay: The membranes were assembled into the flat-bed bioreactor. The cell-seeded membrane has an area of ~30 $cm^2$. The bioreactors were conditioned by injecting medium through the bioreactor's inlets, and the medium-filled bioreactor was incubated for 60 min at 37° C. in a 5% $CO_2$ atmosphere. The medium was discarded afterwards. Cells were trypsinized, and $1\times10^7$ HK-2 cells were seeded onto the membrane by injecting the cell suspension into the bioreactor, ensuring that no bubbles were present. The cell-seeded bioreactor was then incubated for 5 h at 37° C. in a 5% $CO_2$ atmosphere under static conditions to allow cell attachment. In the case of HPTCs, $4\times10^6$ cells were seeded. The bottom chamber was filled with 10 ml of medium. HPTCs were incubated for 4 h or overnight (for the GGT assay) for cell attachment. After cell attachment, the bioreactors were connected to a pump for perfusion at a medium flow rate of 0.5 ml/min or 80 microliters/min (for the GGT assay). For the GGT assay, a second bioreactor with NIH/3T3 cells was seeded and run in parallel.

For assaying GGT activity, the bioreactor was perfused with phenol red-free cell culture medium supplemented with 20 mM of glycyl-glycine and 1 mM of L-gamma-glutamyl-(p-nitroanilide) obtained from Sigma-Aldrich. The bioreactor was perfused with this medium for 4 h for conditioning, and the assay was performed with medium collected during the following hour. The concentration of 4-nitroanilide was determined with a microplate reader at 405 nm.

Immunostaining: For immunostaining, the membranes with the cells were washed with phosphate-buffered saline (PBS) and fixed with 3.7% formaldehyde/PBS for 10 min at room temperature. Indirect immunostaining of the tight junction protein zonula occludens (ZO)-1 and α (alpha)-smooth muscle actin (α-SMA) was performed. Cell nuclei were stained with 4′,6′-diamidino-2′-phenylindole (DAPI). For the assessment of immunostaining results in each case, three replicas were overall inspected visually, and multiple images were taken from different regions of each sample. Most of the experiments were repeated at least once and different batches of HPTCs were used.

ECM-coating and double-coating with DOPA and collagen type IV: Murine collagen type I (750 micrograms/ml; Allergan, Fremont, Calif., USA), human placental collagen type IV (150 micrograms/ml, Merck), or human placental collagen type IV mixed with laminin (Sigma-Aldrich, 100 micrograms/ml of laminin mixed with 150 micrograms/ml of collagen type IV) were used. Membranes were coated with ECM components according to the procedure described in H. Zhang, et al., "The impact of extracellular matrix coatings on the performance of human renal cells applied in bioartificial kidneys," *Biomaterials*, 2009, 30(15), 2899-2911, incorporated herein by reference. Briefly, the ECM components were diluted to their final concentrations with cell culture medium. The coating solution was added to the membrane and dried overnight, e.g., in a laminar flow hood. This method was applied to untreated membranes, or membranes that have been coated with DOPA according to the procedure described in Table 1.

Quantification of the amounts of fluorescein isothiocyanate (FITC)-conjugated collagen type IV adsorbed onto different substrates: The experiments were performed with human placental collagen type IV conjugated with FITC (Invitrogen). Briefly, FITC-labeled collagen type IV was used in order to quantify the amount of collagen type IV adsorbed on untreated and DOPA-coated PES/PVP membranes. 150 micrograms/ml of FITC-labeled collagen type IV (human placenta, Invitrogen) was adsorbed on the untreated and DOPA-coated PES/PVP membranes in 96-well tissue culture plates (Nunc) for 1 h at 37° C. TCPS served as a control. To dissociate loosely bound protein and to prevent rebinding, the substrates were washed three times with PBS before fluorescence reading in a microplate reader (Tecan Safire™, Männedorf, Switzerland) at excitation and emissions wavelengths of 485 nm and 530 nm, respectively. Three replicas were assessed. Known amounts of FITC-labeled collagen type IV were used to generate a standard curve.

Cell attachment to PES/PVP membranes: Membrane attachment of HK-2 cells was determined using the TBO assay. Briefly, untreated and surface-treated PES/PVP membranes were cut to fit into the wells of 96-well plates (Nunc). HK-2 cells were seeded on the membranes at a density of $6 \times 10^4$ cells/sample. Cells were allowed to attach for 1 h, and non-adherent cells were rinsed from the sample. Adherent cells were fixed with 4% paraformaldehyde, and stained with 0.5% TBO in 4% paraformaldehyde. The stain was solubilized with 1% sodium dodecyl sulfate, and the absorbance was measured at 630 nm using a microplate reader (Tecan Safire™, Männedorf, Switzerland).

The 3-(4,5-dimethylthiazol-2-yl)-5-(3-carboxy-methoxyphenyl)-2-(4-sulfophenyl)-2H tetrazolium inner salt (MTS) assay (Promega, Madison, Wis., USA) was performed according to the instructions provided by the manufacturer. Briefly, at each time point, cells were incubated in complete medium with MTS reagent at a volume ratio of 19:1. After 1 h of incubation, the optical density (OD) was measured at 490 nm. The results presented show the absorbance readings after subtracting the values obtained with blank wells.

Imaging: Epifluorescence imaging was performed by using a Zeiss AxioObserver Z1 (Carl Zeiss, Jena, Germany) or an Olympus BX-DSU (Olympus, Tokyo, Japan) fluorescence microscope. For scanning electron microscopy (SEM) of cells, the samples were first fixed in 2.5% glutaraldehyde in PBS, and then dehydrated in an ethanol series (30%, 70%, 80%, 90%, 95%, 3×100%, 30 min each). The samples were subsequently dried in an Autosamdri 825 critical point dryer (Tousimis Inc., Rockville, Md., USA). Finally, the samples were sputtered with gold, and SEM was conducted with a JSM-7400F field emission scanning electron microscope (JEOL, Tokyo, Japan). SEM of membranes was performed with the same microscope after freeze-drying the samples overnight and sputter coating with platinum.

Statistics: All statistical analyses were performed using Microsoft® Excel (Microsoft Corp., Redmond, Wash.). Student's two-tailed t-test was used for determining the significance levels.

HPTC performance on polymeric membranes: In a first series of experiments, the performance of HPTCs was tested on various polymeric membranes. Cell performance was tested for a time period of three weeks to find out whether certain materials might be more suitable for long-term applications. The membrane materials tested included PSF/PVP, which are currently widely used for hemodialysis or hemo filtration and have been applied in BAKs. In addition, membranes of PES/PVP and regenerated cellulose (RC), which have also been used for hemodialysis or hemo filtration, were also studied. Furthermore, membranes of poly (ether imide)-FC (PEI-FC) were also tested. Poly(ether imide)-based membranes appeared to be well-suited for the construction of biohybrid organs. As a positive control, PET Transwell® membranes were employed, which are frequently used for in vitro cell culture in co-culture systems and also with renal cells. PET Transwell® membranes were treated with oxygen plasma to enhance biocompatibility. All other membranes tested were not subjected to any surface treatments.

The HPTCs were cultivated for three weeks (seeding density: $1 \times 10^5$ cells/cm$^2$) on different polymeric membranes consisting of the materials indicated. All materials were uncoated except tissue culture polystyrene (TCPS), which was used as another positive control and was coated with collagen type IV. ZO-1 and a (alpha)-SMA were detected by immunostaining (DAPI). Substantial amounts of a (alpha)-SMA-expressing myofibroblasts were detected on PET Transwell® membranes. In each case, three replicas were assessed. From each sample, multiple images were captured from different areas. Representative images are shown in FIG. 2. Scale bar is 50 micrometers.

After a cultivation period of three weeks, only a few cells were present on PSF/PVP, PES/PVP, RC, and PEI-FC membranes (FIG. 2A-2D). In contrast, a substantial number of cells and monolayer formation were observed on PET Transwell® membranes, the positive control (FIG. 2E). However, epithelial differentiation was not sufficient, as indicated by the ZO-1 immunostaining patterns (the tight junctional component ZO-1 is a marker for epithelial differentiation, and chicken wire-like ZO-1 immunostaining patterns reflect proper tight junction formation). Also, a substantial number of a (alpha)-SMA-expressing myofibroblasts was present on PET Transwell® membranes (FIG. 2E; α (alpha)-SMA-expressing myofibroblasts appear to arise in HPTC in vitro cultures by a process of epithelial-to-mesenchymal transition).

In contrast, HPTCs formed differentiated epithelia on collagen type IV-coated tissue culture polystyrene (TCPS), which served as another positive control (FIG. 2F). These epithelia showed extensive tight junction formation, as indicated by the chicken wire-like ZO-1 immunostaining patterns. HPTC epithelia showing chicken wire-like ZO-1 immunostaining patterns were polarized and displayed an apical brush border. These features may be important for proper cell performance in BAKs. TCPS was treated with oxygen plasma to improve biocompatibility, and differentiated epithelia of HPTCs can be maintained for time periods of ~2-3 weeks on collagen type IV-coated TCPS.

HPTC performance on ECM-coated membranes: The findings outlined above showed that HPTC performance did not appear sufficient on the conventional polymeric membrane materials that were tested. The results also suggested that surface treatments and suitable extracellular matrix (ECM) coatings might improve HPTC performance. In order to investigate whether ECM coatings could sufficiently improve HPTC performance on membrane materials used for hemodialysis or hemofiltration, cell growth on uncoated or ECM-coated PES/PVP membranes was analyzed. Collagen type I and collagen type IV were used as coating materials as the highest rates of human renal proximal tubule cell proliferation were previously observed on these ECM coatings. Specifically, good results were obtained with collagen type IV coatings in terms of HPTC differentiation and the maintenance of differentiated HPTC epithelia. In addition, a mixture of collagen type IV and laminin, which are both basal lamina components, was tested. Control experiments with FITC-labeled collagen type IV showed that the adsorption of this coating material to PES/PVP membranes was at least as good as to TCPS (FIG. 3). As a control for the cell proliferation experiments, uncoated and ECM-coated PET Transwell® membranes, on which HPTCs proliferated well (FIG. 2E), were used.

FIG. 3 shows adsorption of FITC-conjugated collagen type IV on different substrates. The bars (mean±SD, n=3) indicate the amounts of FITC-conjugated collagen type IV adsorbed to the surfaces of TCPS, and untreated or DOPA-coated PES/PVP membranes. Significant differences are denoted by the asterisks (*: $p<0.05$, ***: $p<0.001$).

The HPTCs seeded at a density of $1\times10^5$ cells/cm$^2$ were cultivated for up to four weeks on PES/PVP or PET Transwell® membranes. The membranes were uncoated or coated with collagen type I, collagen type IV, or a mixture of collagen type IV and laminin. The cell numbers were determined weekly by cell counting using a corresponding subset of the samples cultivated in parallel. The four white and grey bars in each group (FIG. 4) indicated the cell numbers on PES/PVP and PET Transwell® membranes, respectively, at week 1, 2, 3 and 4 (from left to right, mean±standard deviation (SD), n=3).

Figure 4:
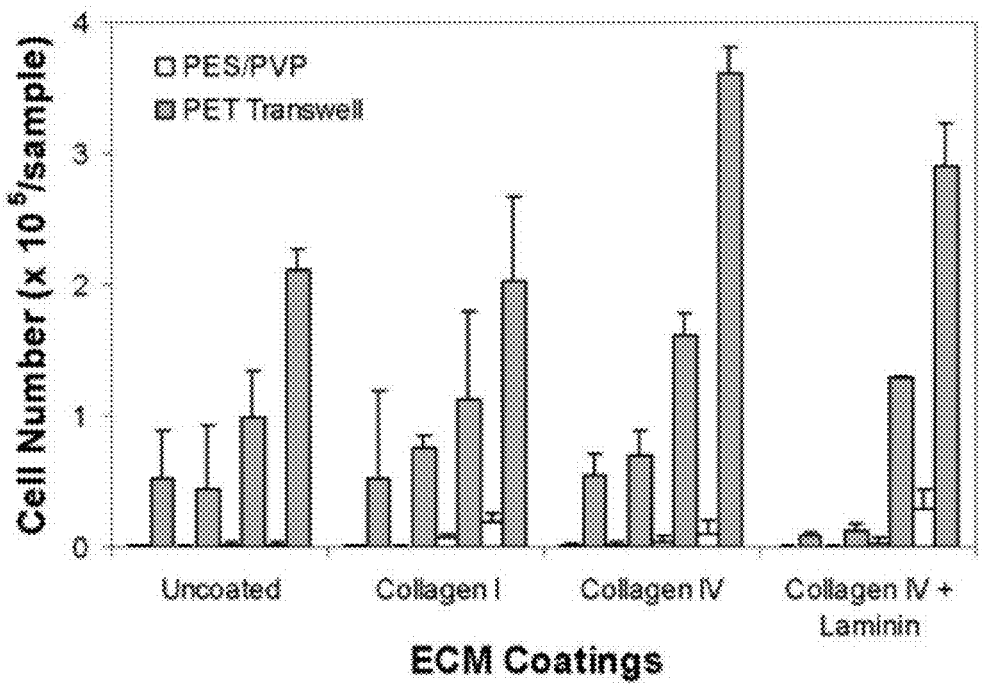
FIG. 4 is a graph that illustrates human renal proximal tubule cell proliferation on certain membranes, in various embodiments of the invention.

The results showed that HPTC performance was much more influenced by the underlying membrane material than by the ECM coating. HPTCs proliferated well on PET Transwell® membranes, and this applied to uncoated as well as to coated membranes, although some impact of the different ECM coatings on growth rates was observed (FIG. 4). In contrast, cell numbers always remained very low on PES/PVP membranes, for both the uncoated and the coated membranes (FIG. 4). Again, some impact of the ECM coatings was observed, and during the second half of the incubation period, cell numbers were higher on the ECM-coated PES/PVP membranes, as compared to the uncoated membranes. Nevertheless, cell numbers remained in all cases very low, and the results obtained with the ECM-coated PES/PVP membranes were not sufficient for the applications discussed above. The same applied to PSF/PVP membranes coated with collagen type IV or other ECM coatings (data not shown). In addition, immunostaining and visual inspection of ECM-coated PET Transwell® membranes revealed that in this case, ECM coating could not adequately improve cell differentiation (data not shown). Thus, together, the results show that the membrane material has a major impact on HPTC performance, even after the application of ECM coatings. Non-HPTC-compatible membranes could not be significantly improved by applying an appropriate ECM coating.

Effects of surface treatments on the hydrophilicity of PES/PVP membranes: As HPTCs did not perform well on a variety of conventional polymeric membrane materials including PES/PVP and PSF/PVP, which are of interest for applications in BAKs, and as sufficient improvements could not easily be achieved by applying ECM coatings, various surface modifications of the conventional membrane materials were studied. First, the effects of surface modifications were examined. In an initial series of experiments, water contact angles were measured to determine the effects of various surface treatments on the hydrophilicity of PES/PVP membranes. HPTCs grew and differentiated well on hydrophilic glass or TCPS surfaces, suggesting that increasing the surface hydrophilicity might help to improve HPTC performance.

Various treatments and components (see Table 1) were selected for the following reasons. Poly(maleic anhydride-alt-1-octadecene) (PA-18) is an amphiphilic copolymer. Coating of a hydrophobic surface with this copolymer in an aqueous environment could lead to an ordered arrangement of the amphipilic molecules, resulting in the exposure of their hydrophilic portions, thus rendering the surface more hydrophilic. Poly-L-lysine (PLL) is positively charged, and is frequently used to improve cell adhesion to substrate surfaces. Hydrogen peroxide is a strongly oxidizing agent, which introduces hydrophilic functional groups. Oxygen plasma treatment is known to introduce carboxylic acid and hydroxyl groups to membrane surfaces, and is often used to improve the cytocompatibility of polymeric substrates. 3,4-Dihydroxy-L-phenylalanine (DOPA) is a compound secreted by mussels for strong adhesion to wet surfaces. It can form a thin adhesive polymeric film on different substrates.

Figure 5:
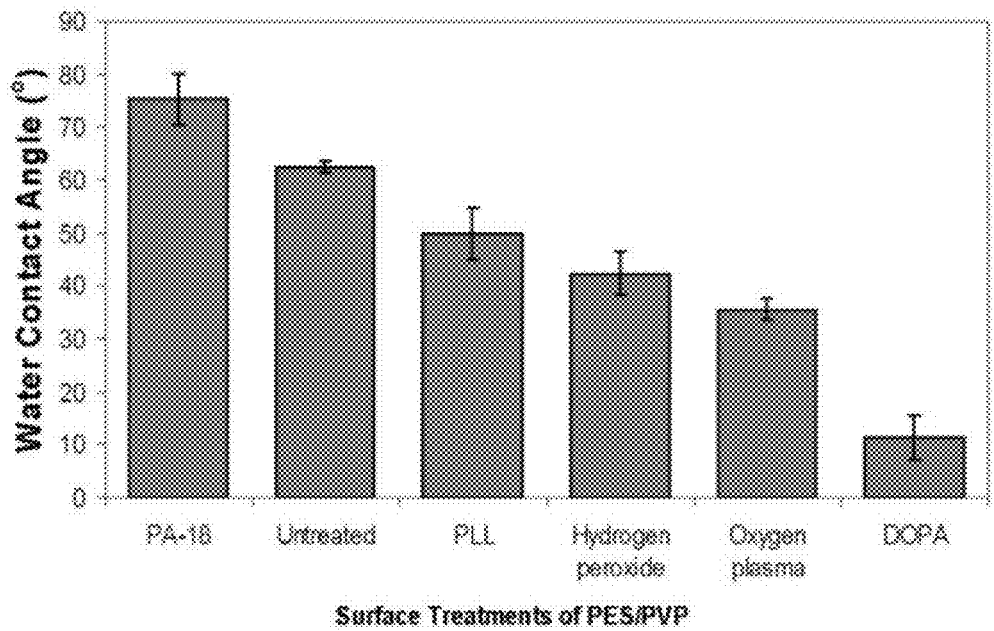
FIG. 5 is a graph that illustrates the effect of certain surface treatments on hydrophilicity of a membrane in accordance with certain embodiments of the invention.

FIG. 5 shows the water contact angles measured after applying the various treatments to PES/PVP membranes. The water contact angle of untreated PES/PVP was 62.5°±1.1°, whereas that of TCPS (the "gold standard" for cell culture) was ~45°. The water contact angle of PES/PVP membranes could be systematically changed by applying the various surface treatments (FIG. 5). PA-18-treated PES/PVP was even more hydrophobic (water contact angle of 75.4°±4.8°) than the untreated PES/PVP. In contrast to PA-18, the other surface treatments resulted in more hydrophilic membrane surfaces, as compared to untreated PES/PVP. PLL treatment somewhat reduced the water contact angle to ~50°. Hydrogen peroxide and oxygen plasma treatments led to a further reduction of the contact angle to ~40°. The largest change in surface hydrophilicity was induced by DOPA treatment, which decreased the contact angle to 15°. In FIG. 5, the bars indicate the contact angles of water droplets on untreated or treated PES/PVP membranes (n=4, mean±SD).

Figure 6:
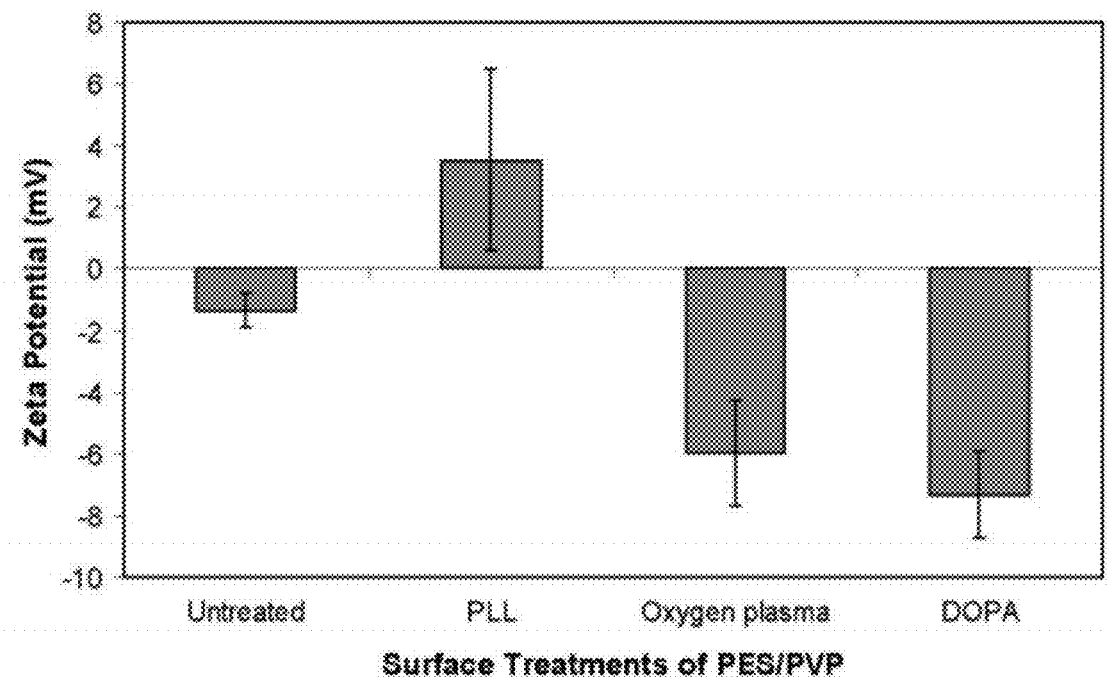
FIG. 6 is a graph that shows zeta potentials of certain membranes, in accordance with certain embodiments of the invention.

The effects of various treatments on the surface charge and the density of carboxylic acid groups: In a next series of experiments, the zeta potential of untreated PES/PVP membranes was characterized, as well as the effects of various treatments on the surface charge. Untreated PES/PVP membranes have a slightly negative surface charge (FIG. 6). This figure shows zeta potentials of PES/PVP membranes. The bars indicate the zeta potential (mean±SD; n=3) of untreated or treated PES/PVP membranes. As expected, treatment with positively charged PLL resulted in a positive zeta potential of about +4 mV. In contrast, oxygen plasma-treated and DOPA-treated PES/PVP membranes displayed more negative zeta potentials of about −6 to −7 mV (FIG. 6), suggesting the introduction of negatively charged functional groups, such as carboxylic acid groups. Hence, the densities of carboxylic acid groups on the surfaces of untreated and treated PES/PVP membranes were examined using the TBO dye assay.

Figure 7A:
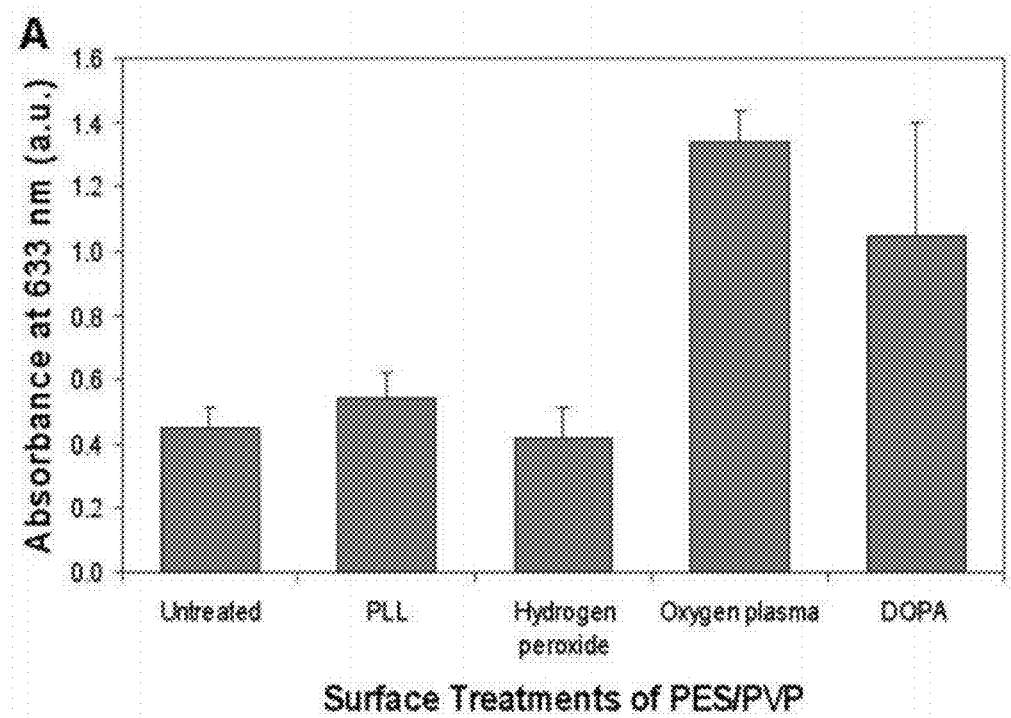
FIGS. 7A-7C are graphs that illustrate the effects of certain surface treatments on the introduction of carboxylic acid groups on the surfaces of certain membranes, in accordance with some embodiments of the invention.
Figure 7B:
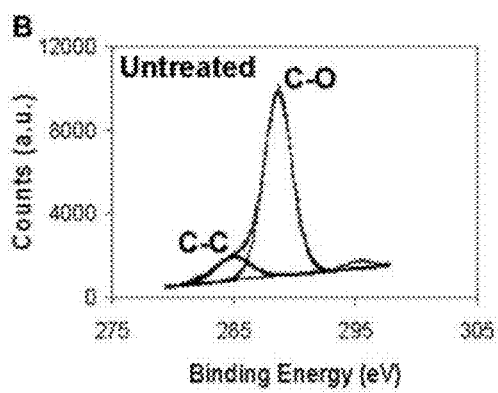
Figure 7C:
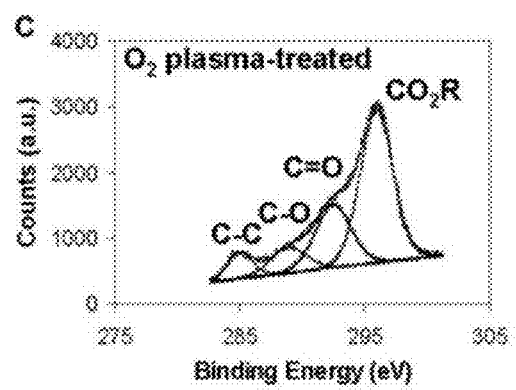

FIG. 7 shows the introduction of carboxylic acid groups on the surfaces of PES/PVP membranes. FIG. 7A shows the content of carboxylic groups on the surface of PES/PVP membranes as determined using the TBO assay. The bars indicate the absorbance at 633 nm (mean±SD, n=3). FIGS. 7B and 7C show high-resolution XPS spectra of untreated (FIG. 7B) and oxygen plasma-treated (FIG. 7C) PES/PVP membranes.

FIG. 7A thus illustrates that oxygen plasma treatment introduced the highest density of functional groups, which were confirmed by XPS spectroscopy to be carboxylic acid groups (FIGS. 7B and 7C). The high-resolution XPS C1s spectra showed the presence of carboxyl and carbonyl groups on the oxygen plasma-treated PES/PVP (FIG. 7C), which were not detected on the untreated sample (FIG. 7B). The TBO dye assay revealed that a high density of functional groups was also introduced by the DOPA treatment (FIG. 7A). This could be attributed to the carboxylic acid group associated with the DOPA molecule contained. As expected, PLL coating and hydrogen peroxide treatment did not lead to significant changes in the surface density of functional groups.

Figure 8:
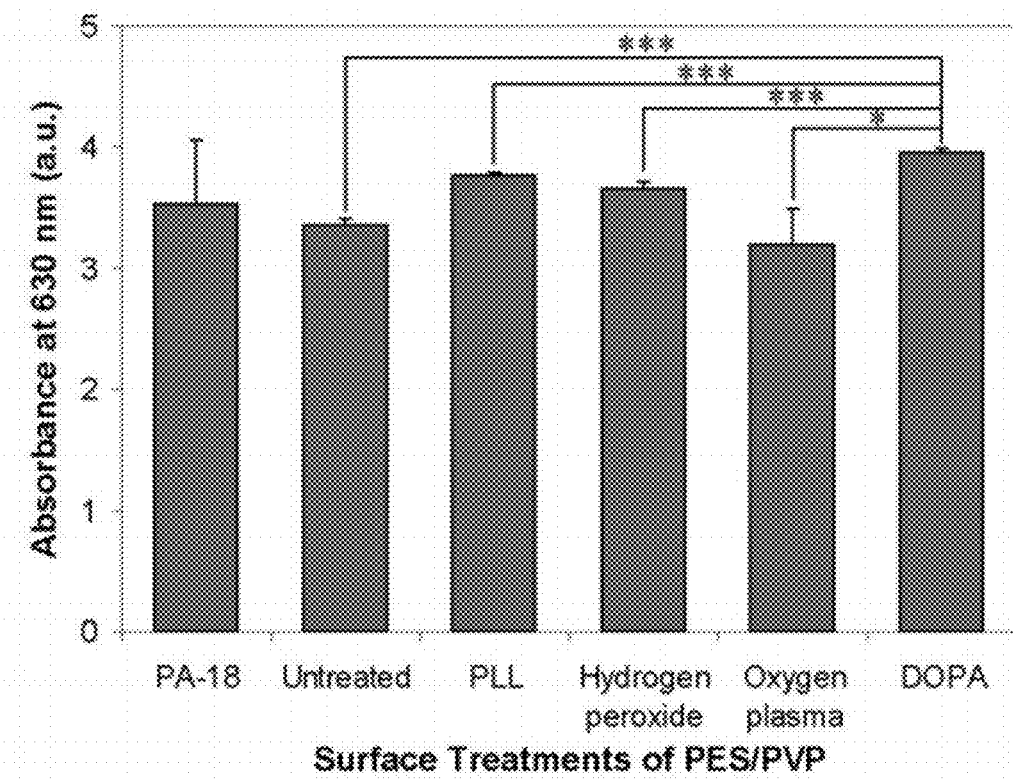
FIG. 8 is a graph that illustrates the adhesion of HK-2 cells to certain membranes, in one embodiment of the invention.

Human proximal tubule cell attachment: Next, the different treatments and changes in surface properties and how they affected human proximal tubule cell attachment was tested. The assays were performed with HK-2 cells (human proximal tubule cell line), and cell attachment to the membranes was quantified by using the TBO assay. As shown in FIG. 8, good results were obtained with DOPA treatment, and cell attachment was significantly enhanced as compared to untreated PES/PVP membranes and membranes treated with PLL, hydrogen peroxide or oxygen plasma. In FIG. 8, cell adhesion was determined 1 h after cell seeding using the TBO assay (mean±SD, n=3). The asterisks indicate significant differences (***: $p<0.001$, *: $p<0.05$).

These results also showed that although both DOPA and oxygen plasma treatment led to a net negative surface charge (FIG. 6) and increased the density of carboxylic acid groups (FIG. 7), cell attachment to DOPA-treated PES/PVP membranes was significantly enhanced as compared to oxygen plasma-treated membranes (FIG. 8). This suggested that the high degree of cell attachment to DOPA-treated surfaces was due to the introduction of other functional groups, such as amino groups, present in the DOPA molecule. As good results in terms of cell attachment were obtained with DOPA-coated membranes, but the effects of DOPA coating on renal cell performance during more extended time periods were unclear, this aspect was further investigated in the following experiments.

Figures 9A, 9B:
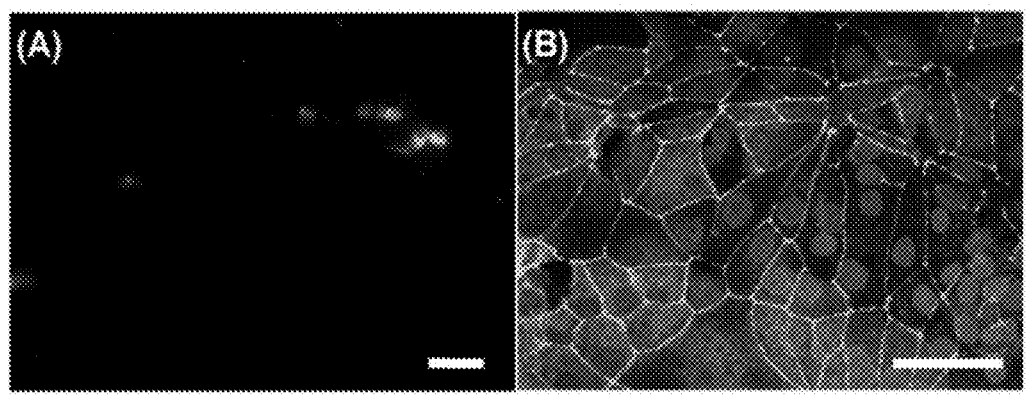
FIGS. 9A-9B are photomicrographs that illustrate the proliferation and differentiation of HK-2 cells on certain membranes, in certain embodiments of the invention.

Proliferation and differentiation of proximal tubule cells on DOPA-treated membranes: First, proliferation and differentiation of HK-2 cells was addressed. FIG. 9B shows that these cells formed a confluent differentiated epithelium on DOPA-coated PES/PVP membranes after 1 week of in vitro culture. In contrast, only a few single cells could be found on the untreated PES/PVP membranes (FIG. 9A).

In particular, HK-2 cells were seeded ($1\times10^5$ cells/cm$^2$) onto untreated (FIG. 9A) or DOPA-coated PES/PVP membranes (FIG. 9B), and the membranes were imaged after one week of in vitro culture. ZO-1 was detected by immunostaining. In each case, three replicas were assessed. From each sample, multiple images were taken. Representative images are shown. Scale bar is 50 micrometers.

Nevertheless, HK-2 cells are functionally not always equivalent to HPTCs, which are of major clinical importance. Therefore, proliferation and differentiation of HPTCs was also characterized. First, proliferation during a cultivation period of 1 week was addressed. FIG. 10C shows that HPTC numbers dropped substantially on untreated PES/PVP membranes during the first two days after seeding, and remained constantly low for the rest of the cultivation period. In contrast, after a slight decrease in cell numbers during the first two days after seeding, exponential growth was observed for the rest of the cultivation period on DOPA-coated PES/PVP membranes. These data were consistent with visual impressions (FIGS. 10A and 10B) and the initial findings discussed above (FIG. 2). Visual inspection also revealed many dead and compromised cells on the untreated membranes, which suggested that the low cell numbers observed here were not only due to weak cell attachment.

Figures 10A, 10B:
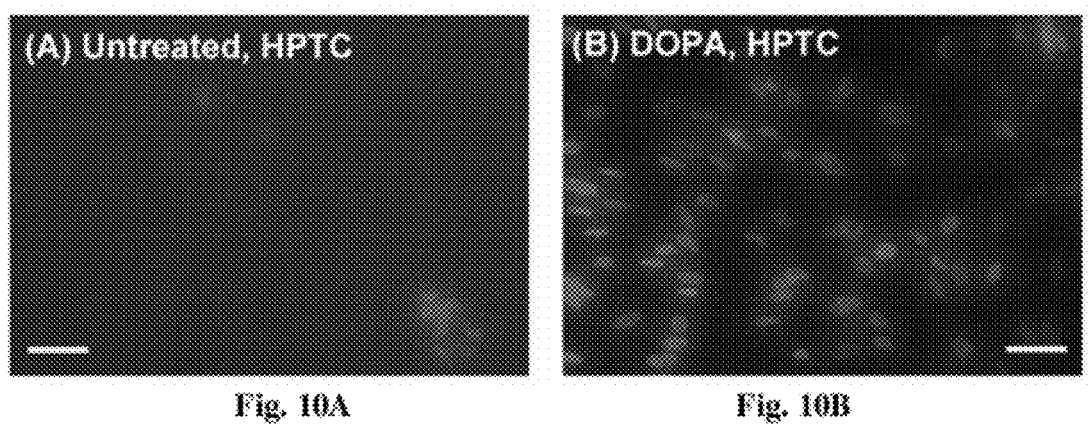
FIGS. 10A-10C are photomicrographs (FIGS. 10A and 10B) and a graph (FIG. 10C) that show the proliferation of primary human renal proximal tubule cells on certain membranes, in accordance with one embodiment of the invention.
Figure 10C:
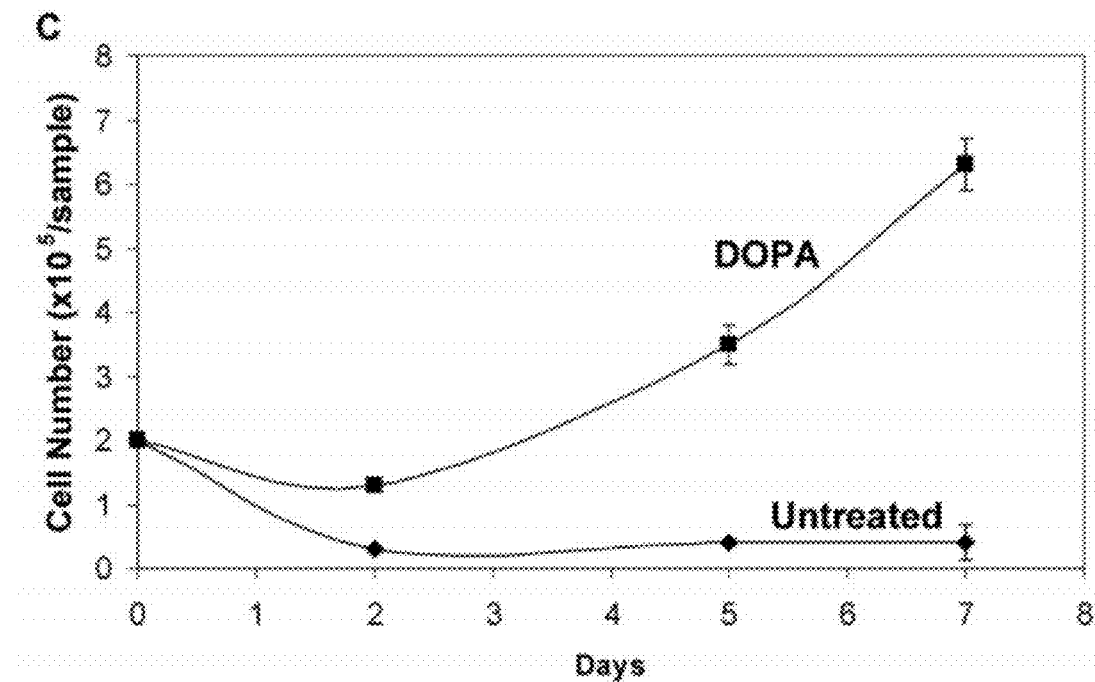

FIGS. 10A and 10B are micrographs of DAPI-stained nuclei of HPTCs captured after one week of in vitro culture on untreated (FIG. 10A) and DOPA-coated (FIG. 10B) PES/PVP membranes (seeding density of $5\times10^4$ cells/cm$^2$). Scale bar is 50 micrometers. In FIG. 10C, HPTC numbers were counted at 0, 2, 5 and 7 days after cell seeding on the untreated or DOPA-coated PES/PVP membranes (mean±SD, n=3).

HPTC performance on DOPA-coated and DOPA/collagen type IV-coated membranes: Next, formation of differentiated epithelia by HPTCs was investigated. ZO-1 immunostaining patterns indicated that HPTCs did not form properly differentiated epithelia on DOPA-coated PES/PVP membranes (data not shown), in contrast to HK-2 cells (FIG. 9). It was also found previously that HPTCs did not perform well on ECM-coated PES/PVP (FIG. 4). However, given the findings that HPTC proliferation and monolayer formation was improved on DOPA-coated PES/PVP (FIG. 10), and that collagen type IV promoted the formation of differentiated epithelia by HPTCs if the cells grew on a suitable substrate, it was next examined whether HPTCs might form differentiated epithelia on PES/PVP membranes that were first coated with DOPA and subsequently coated with a layer of collagen type IV. Control experiments performed with FITC-conjugated collagen type IV showed that DOPA coating significantly increased the amount of adsorbed collagen type IV, as compared to untreated PES/PVP and TCPS (FIG. 3).

Figures 11A, 11B, 11C, 11D:
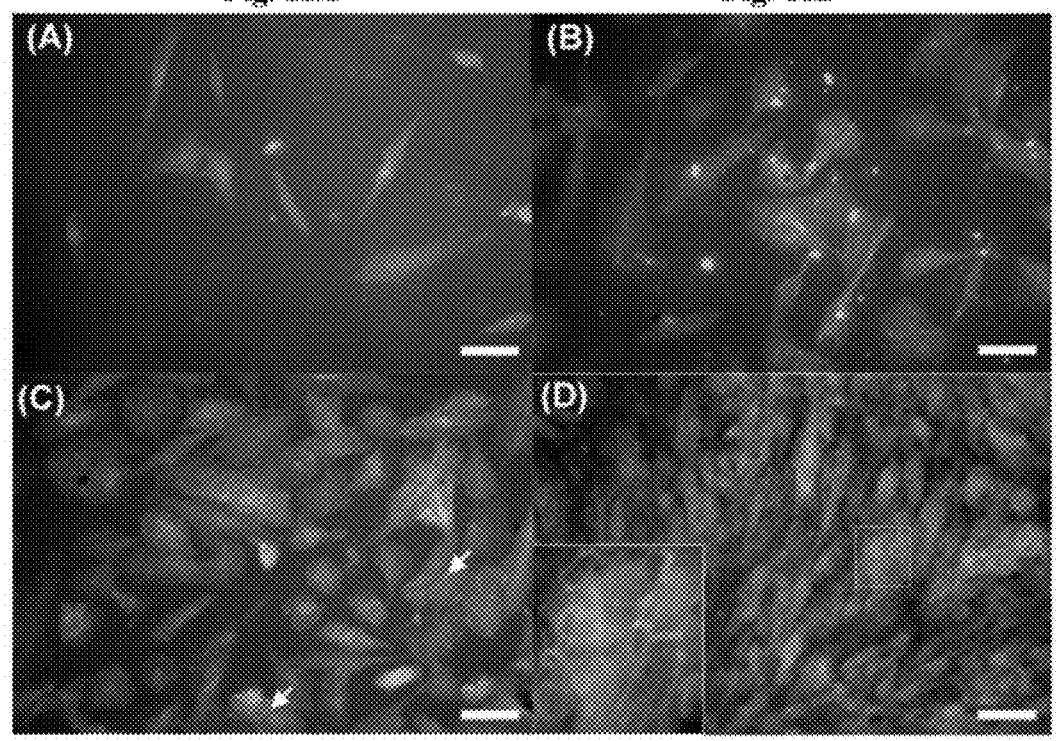
FIGS. 11A-11D are photomicrographs that illustrate the performance of primary human renal proximal tubule cells on certain coated membranes in various embodiments of the invention.

The formation of differentiated epithelia by HPTCs, which had been cultivated for 1 week on double-coated membranes, was then addressed. The HPTCs were imaged after one week of in vitro culture (seeding density of $5\times10^4$ cells/cm$^2$) on untreated (FIG. 11A), collagen type IV-coated (FIG. 11B) and DOPA- and collagen type IV-coated (FIG. 11C) PES/PVP membranes. FIG. 11D shows the result obtained with DOPA- and collagen type IV-coated PSF/PVP membranes (same seeding density and cultivation period). ZO-1 was detected by immunofluorescence (ZO-1 and DAPI). The arrows in FIG. 11C point to some areas where tight junction formation occurred. However, cells were still subconfluent after one week of cultivation on double-coated PES/PVP membranes, and did not display extensive tight junction formation. In contrast, HPTCs were confluent after one week of cultivation on double-coated PSF/PVP membranes, and extensive tight junction formation occurred (FIG. 11D). The inset in FIG. 11D shows an enlargement of the boxed area where tight junction formation is visible.

Although extensive tight junction formation occurred, tight junctions are not visible in all areas in FIG. 11D, since the densely populated membrane surface was not completely planar. Therefore, different areas resided in different focal planes. In each case, three replicas were assessed. From each sample, multiple images were captured from different areas. Representative images are shown. Scale bar is 50 micrometers.

FIG. 11C shows that increased cell numbers and enhanced tight junction formation were observed on DOPA/collagen type IV-coated PES/PVP membranes, as compared to the untreated or collagen type IV-coated PES/PVP membranes (FIGS. 11A and 11B). However, no confluent epithelia were formed 1 week after cell seeding. As HPTC performance was influenced by the underlying membrane material and the surface coatings, whether cell performance could be further improved by using another membrane material, i.e. PSF/PVP, which had already been applied in BAKs, was also investigated. FIG. 11D shows that HPTCs formed a well-differentiated and confluent epithelium on DOPA/collagen type IV-coated PSF/PVP membranes 1 week after seeding. In contrast, HPTC performance was poor on uncoated or collagen type IV-coated PSF/PVP membranes (FIG. 2 and data not shown).

Together, the results showed that single coating of PES/PVP or PSF/PVP membranes with either suitable ECM components or other molecules impacting proximal tubule cell behavior did not improve HPTC performance sufficiently for applications in BAKs. However, double coating of PSF/PVP membranes with DOPA and collagen type IV led to the formation of differentiated epithelia by HPTCs, which was important for applications in BAKs.

HPTC performance on pure PES and PSF membranes: In FIG. 12, HPTCs were cultivated for 1 week (FIGS. 12A-12C) or 3 weeks (FIG. 12D) on membranes of pure PSF (seeding density of $5\times10^4$ cells/cm$^2$). ZO-1 was detected by immunostaining (DAPI). PSF membranes were uncoated (FIGS. 12A and 12D), coated with collagen type IV (FIG. 12B), or double-coated with DOPA and collagen type IV (FIG. 12C).

Current synthetic hemodialyzer membranes based on either PSF or PES typically contain PVP as an anti-fouling agent. However, PVP might have negative effects on renal cell attachment, growth, and survival. Indeed, cell growth, survival and differentiation were greatly improved on pure PES (data not shown) and PSF membranes (as compared to PVP-containing membranes; FIGS. 2 and 12D), even when these pure membranes were uncoated. HPTC growth and survival could be further improved by a single collagen type IV coating or a double coating with DOPA and collagen type IV (FIGS. 12A-12C). Cell growth on uncoated pure PSF or PES membranes was relatively slow, and the formation of a differentiated epithelium could be only observed after a cultivation period of ~2-3 weeks (FIG. 12).

These experiments addressed the performance of human renal proximal tubule cells on polymeric membranes, which were either untreated or subjected to different surface treatments and coating procedures. It was found that HPTCs did not form differentiated epithelia on most of the untreated membranes, including RC, PSF/PVP and PES/PVP membranes. Membranes of these materials have been used for hemodialysis or hemo filtration, and PSF/PVP membranes have also been applied in BAKs after ECM coating. All surface treatments tested herein and having a single coating with DOPA or an ECM did not sufficiently improve HPTC performance on these membranes. These findings suggested that ECM-coated PSF/PVP membranes may not be suitable for applications in the bioreactor unit of BAKs, at least not with HPTCs. It was also found that the human immortalized proximal tubule cell line HK-2 formed differentiated epithelia on DOPA-coated PES/PVP membranes, in contrast to HPTCs. This again underlined the different behavior of HPTCs and established cell lines.

It was also found that cell behavior was often impacted by a combination of the membrane materials employed and the coatings applied, when single coatings were used. This might be because single coatings could still allow some interactions between the membrane material and the cell surface, which could compromise cell behavior. Double coatings with different coating materials showing different types of interactions with the membrane surface might render the membrane surface less accessible to cells, and this may explain why double coating with DOPA and collagen type IV markedly improved HPTC performance on PES/PVP and PSF/PVP membranes. It turned out that PVP was an important component in these membranes, as HPTCs formed differentiated epithelia on pure PSF or PES membranes, although epithelium formation was relatively slow.

The data suggest that hydrophilicity may be an important membrane feature. HPTCs formed differentiated epithelia on hydrophilic TCPS and glass surfaces. Although this also occurred on PSF and PES membranes, epithelium formation was much slower on these hydrophobic substrates, suggesting slower cell proliferation. It should be noted that of all the treatments examined, DOPA coating led to the most pronounced increase in hydrophilicity. Positively charged surfaces might promote HPTC adhesion, but not the formation of differentiated epithelia. This was suggested by the fact that HPTCs did not form differentiated epithelia on TCPS coated with poly-L-lysine. Thus, hydrophilic and negatively charged surfaces might be more suitable.

The results also suggested that neither carboxylic acid groups, nor biological cell adhesion or signaling molecules, were critical. It was also important to note that the surfaces designed for applications with HPTCs should have good adhesive properties. In fact, the problems caused by PVP appeared to be due to its anti-adhesive effects when introduced into PSF membranes. PVP in the cell culture medium did not compromise HPTC performance. HPTCs appeared to be particularly sensitive to the surface adhesiveness of substrates, as other renal cell types (e.g. MDCK and LLC-PK1) performed well on PVP-containing and other less adhesive materials.

In summary, it appears that substrate surfaces for HPTCs are advantageously hydrophilic, negatively charged, and adhesive. These properties seem to be important but are not sufficient to generate properly differentiated HPTC epithelia. This is suggested by the fact that single DOPA-coated membranes display these properties and sustain HPTC attachment and proliferation, but not the formation of differentiated epithelia by this cell type. This study thus demonstrates that ECM coatings can be applied to promote differentiation under conditions where adhesion, growth, and survival are not compromised.

The notion that membrane materials for HPTCs should have good adhesive properties suggests that a membrane with both surfaces composed of the same material might not be useful for BAK applications, as the blood-exposed surface should be anti-adhesive. The concept of asymmetric membranes is important, and the hemocompatible non-adhesive side could also provide the required mechanical strength.

These results show that conventional materials used in BAKs thus far are not well suited for applications with HPTCs. The hemodialyzer membranes were optimized for hemocompatibility, but not for the growth of complex primary cells. Differentiated epithelia were successfully formed by HPTCs on pure PSF or PES membranes (although requiring longer time intervals), and PSF/PVP membranes with a double coating of DOPA and an ECM.

Example 2

These experiments illustrate that the coating of a membrane with an adhesive as discussed herein may not substantially adversely affect water flux through the membrane. An experiment was performed with commercial polyethersulfone (PES) membranes from Millipore with a molecular weight cut-off of 30 kDa, as shown in FIG. 13. The results obtained with uncoated (left-hand bar) and coated (right-hand bar) PES membranes were not significantly different (Student's t-test, p>0.05). The experiment has been repeated and consistently no differences between coated and uncoated membranes were observed.

Further experiments to determine the potential impact on membrane permeability were carried out using non-coated Vivaspin™ columns as control and Vivaspin™ columns coated with DOPA and collagen type IV. The Vivaspin™ columns used comprised of PES membrane with a molecular weight cut off of 30,000 kDa. An example Vivaspin™ column is shown in FIG. 14A. 3 mg of urea solution was added to the upper compartment of the Vivaspin™. Cell culture media was added to the lower compartment. A magnetic stirrer was used to generate force in the upper compartment. The set up was left overnight. The amount of urea in the upper and lower compartment was measured using an i-Stat analyzer for both coated and uncoated spin columns. The percentage of urea in the respective compartments was calculated as: (amount of urea in the compartment/3 mg of urea)×100.

Ideally, most of the urea should flow through to the lower compartment. As indicated in Table 2, 90% of the urea that was initially added was found in the lower compartment of an uncoated column. In comparison, 68% of the urea was found in the lower compartment of the coated column suggesting that the flow might be a bit slower for the coated columns. Nevertheless, most of the urea was found in the lower compartment for both coated and uncoated columns. In case of the coated columns, 21% (i.e., 100%-11%-68%) of the urea was not found in either the upper or the lower compartment. This could indicate that some of the urea might be stuck to the membranes, particularly because DOPA is an adhesive material.

TABLE 2

|  |  | Uncoated | Coated |
| --- | --- | --- | --- |
| % of Urea | Upper compartment | 6 | 11 |
|  | Lower compartment | 90 | 68 |

5% Bovine Serum Albumin (BSA) was digested using 20 micrograms/ml of Protease K for 1 hour at 55° C. under reducing conditions. 1 mM PMSF (phenylmethylsulfonylfluoride) protease inhibitor was used to stop the digestion.

The digested BSA was added to the upper compartment of the Vivaspin™ column and centrifuged at 3000 g for 3 minutes. Equal amounts of protein from the upper compartment (lanes 3 and 4) or lower compartment (lanes 5 and 6) were loaded onto a gel and the proteins separated using the NuPAGE system (FIG. 14B). Digested BSA which was not applied to the Vivaspin™ columns were used as a control (lane 2). A prestained Pageruler marker was loaded into lane 1. The experiment was done with both coated (lanes 3 and 5) and uncoated columns (lanes 4 and 6).

Since the molecular weight cut off of the membranes was approximately 30 kDa, protein fragments of sizes greater than 30 kDa should be mostly restricted to the upper compartment (lanes 3 and 4), whereas smaller fragments can pass through the membrane and can be detected in the lower compartment. These results indicate the most of the larger protein fragments are detected in the upper compartment (indicated by the box in lanes 3 and 4), whereas, the lower compartment contains mostly proteins with size smaller than 35 kDa (box in lanes 5 and 6).

These results also suggest that there is no major difference between the coated and uncoated membranes (between lanes 3 and 4, and lanes 5 and 6), indicating that the double coating does not have a negative impact on the molecular weight cut off of the membranes.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:
1. An article, comprising:
a substrate;
a coating positioned on at least a portion of the substrate, the coating comprising a molecule having a catechol moiety and/or a polymer comprising the molecule;
a cell support protein positioned on at least a portion of the coating, wherein at least about 50% of the cell support protein comprises an extracellular matrix protein; and
human cells positioned on at least a portion of the substrate that is coated with the coating and the cell support protein, wherein the human cells are human primary cells, human embryonic stem cells, human mesenchymal stem cells, human induced pluripotent stem cells, and/or human differentiated cells obtained from stem cells.

2. The article of claim 1, wherein the substrate comprises a polymer.

3. The article of claim 1, wherein the coating comprises 3,4-dihydroxy-L-phenylalanine (DOPA).

4. The article of claim 1, wherein the coating comprises poly(dopamine).

5. The article of claim 1, wherein the coating comprises poly(DOPA).

6. The article of claim 1, wherein the extracellular matrix protein comprises a collagen.

7. The article of claim 1, wherein the cell support protein comprises a protein that improves cell differentiation.

8. The article of claim 1, wherein the cell support protein comprises a synthetic peptide.

9. The article of claim 1, wherein the substrate is a membrane.

10. The article of claim 9, wherein the membrane is an ultrafiltration membrane.

11. The article of claim 9, wherein the membrane is a hemodialysis membrane.

12. The article of claim 9, wherein the membrane is a hemofiltration membrane.

13. The article of claim 1, wherein the article is a bioartificial organ.

14. The article of claim 1, wherein the article is a bioartificial kidney.

15. The article of claim 1, wherein the article comprises at least one hemodialysis cartridge.

16. The article of claim 1, wherein the human cells are renal cells.

17. The article of claim 16, wherein the human cells are primary renal proximal tubule cells or stem-cell-derived renal proximal tubule cells.

18. The article of claim 1, wherein the human cells positioned on the substrate are capable of proliferation and/or differentiation.

19. The article of claim 1, wherein the human cells form a confluent, differentiated epithelium on at least a portion of the substrate.

20. The article of claim 1, wherein the coating is an adhesive.

21. The article of claim 1, wherein the substrate comprises a polymer comprising polysulfone, polyethersulfone, and/or polyvinylpyrrolidone.

22. A bioartificial organ, comprising:
a substrate positioned to be fluidly communicable with a source of blood;
a coating positioned on at least a portion of the substrate, the coating comprising a molecule having a catechol moiety and/or a polymer comprising the molecule;
a protein and/or a peptide positioned on at least a portion of the coating, wherein at least about 50% of the protein and/or peptide comprises an extracellular matrix protein; and
human cells positioned on at least a portion of the protein and/or peptide, wherein the human cells are human primary cells, human embryonic stem cells, human mesenchymal stem cells, human induced pluripotent stem cells, and/or human differentiated cells obtained from stem cells.

23. The bioartificial organ of claim 22, wherein the coating is positioned on only one side of the substrate.

24. The bioartificial organ of claim 22, wherein the coating comprises poly(3,4-dihydroxy-L-phenylalanine).

25. The bioartificial organ of claim 22, wherein the substrate comprises a polymer comprising polysulfone, polyethersulfone, and/or polyvinylpyrrolidone.

26. An article, comprising:
a substrate;
a coating positioned on at least a portion of the substrate, wherein the coating comprises a molecule having a catechol moiety and/or a polymer comprising the molecule;
a cell support protein positioned on at least a portion of the coating, wherein the cell support protein comprises a collagen; and
human cells positioned on at least a portion of the substrate that is coated with the coating and the collagen, wherein the human cells are human primary cells, human embryonic stem cells, human mesenchymal stem cells, human induced pluripotent stem cells, and/or human differentiated cells obtained from stem cells.

27. The article of claim 26, wherein the substrate comprises a polymer comprising polysulfone, polyethersulfone, and/or polyvinylpyrrolidone.

28. A method, comprising:
coating at least a portion of a substrate with a coating comprising a molecule having a catechol moiety and/or a polymer comprising the molecule;
coating at least a portion of the coating with a cell support protein, wherein at least about 50% of the cell support protein comprises an extracellular matrix protein; and
seeding human cells on at least a portion of the cell support protein, wherein the human cells are human primary cells, human embryonic stem cells, human mesenchymal stem cells, human induced pluripotent stem cells, and/or human differentiated cells obtained from stem cells.

* * * * *